(12) United States Patent
Kobayashi et al.

(10) Patent No.: US 10,518,487 B2
(45) Date of Patent: Dec. 31, 2019

(54) ARTIFICIAL DEFECT MATERIAL AND MANUFACTURING METHOD OF FRP STRUCTURE

(71) Applicant: MITSUBISHI HEAVY INDUSTRIES, LTD., Tokyo (JP)

(72) Inventors: Seiji Kobayashi, Tokyo (JP); Mitsuyoshi Uematsu, Tokyo (JP); Takahito Shimomukai, Tokyo (JP); Noriya Hayashi, Tokyo (JP); Yuji Maruyama, Tokyo (JP); Hidetaka Hattori, Tokyo (JP); Junko Watanabe, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 277 days.

(21) Appl. No.: 15/518,148

(22) PCT Filed: Oct. 30, 2015

(86) PCT No.: PCT/JP2015/080835
§ 371 (c)(1),
(2) Date: Apr. 10, 2017

(87) PCT Pub. No.: WO2016/068334
PCT Pub. Date: May 6, 2016

(65) Prior Publication Data
US 2017/0274604 A1    Sep. 28, 2017

(30) Foreign Application Priority Data

Oct. 30, 2014   (JP) .................. 2014-221741

(51) Int. Cl.
*B29C 70/22*     (2006.01)
*B29C 70/06*     (2006.01)
(Continued)

(52) U.S. Cl.
CPC ............ *B29C 70/222* (2013.01); *B29C 33/38* (2013.01); *B29C 70/06* (2013.01); *B29C 70/24* (2013.01);
(Continued)

(58) Field of Classification Search
CPC ....... B29C 70/222; B29C 70/06; B29C 33/38; B29C 70/345; B29C 70/446; B29C 70/24;
(Continued)

(56) References Cited

U.S. PATENT DOCUMENTS 5,125,993 A    6/1992   Principe
6,485,594 B1   11/2002  Pabsch et al.
(Continued)

FOREIGN PATENT DOCUMENTS

DE    102008028865 A1   12/2009
EP        0665097 A2     8/1995
(Continued)

OTHER PUBLICATIONS

PCT/IB/338, "Notification of Transmittal of Translation of the International Preliminary Report on Patentability for International Application No. PCT/JP2015/080835," dated May 11, 2017.
(Continued)

*Primary Examiner* — Michael C Miggins
(74) *Attorney, Agent, or Firm* — Manabu Kanesaka; Benjamin Hauptman; Kenneth Berner

(57) ABSTRACT

In an artificial defect material 10 of an FRP structure, a heat-resistant high-linear-expansion material 20 arranged between the layers thermally expands in case of high-temperature shaping of the FRP structure, so that a predetermined shape is shaped between a plurality of layers of the fiber reinforcing base material 14 and the material 20 thermally shrinks at the room temperature after the shaping, so that a space is formed due to the shrinkage difference from the fiber reinforcing base materials 14. The material 20 has a linear expansion coefficient larger than that of the FRP structure by a predetermined value or more, and has the shape keeping property and the heat resistance to endure the shaping temperature.

15 Claims, 19 Drawing Sheets

(51) Int. Cl.
*G01N 29/30* (2006.01)
*B29C 33/38* (2006.01)
*B29D 99/00* (2010.01)
*C08J 5/24* (2006.01)
*G01N 29/06* (2006.01)
*B29C 70/34* (2006.01)
*B29C 70/44* (2006.01)
*B29C 70/24* (2006.01)
*B32B 3/20* (2006.01)
*B32B 5/26* (2006.01)
*B32B 7/04* (2019.01)
*B32B 27/08* (2006.01)
*B32B 27/26* (2006.01)
*B32B 27/28* (2006.01)
*B32B 27/30* (2006.01)
*B32B 27/34* (2006.01)
*B32B 27/36* (2006.01)
*B32B 27/38* (2006.01)
*B32B 27/42* (2006.01)
*B32B 3/28* (2006.01)
*B32B 7/05* (2019.01)
*B29L 31/60* (2006.01)
*B29D 23/00* (2006.01)

(52) U.S. Cl.
CPC .......... *B29C 70/345* (2013.01); *B29C 70/446* (2013.01); *B29D 99/0003* (2013.01); *B32B 3/20* (2013.01); *B32B 3/28* (2013.01); *B32B 5/26* (2013.01); *B32B 7/04* (2013.01); *B32B 7/05* (2019.01); *B32B 27/08* (2013.01); *B32B 27/26* (2013.01); *B32B 27/28* (2013.01); *B32B 27/281* (2013.01); *B32B 27/286* (2013.01); *B32B 27/288* (2013.01); *B32B 27/30* (2013.01); *B32B 27/34* (2013.01); *B32B 27/36* (2013.01); *B32B 27/38* (2013.01); *B32B 27/42* (2013.01); *C08J 5/24* (2013.01); *G01N 29/069* (2013.01); *G01N 29/30* (2013.01); *B29D 23/00* (2013.01); *B29L 2031/601* (2013.01); *B32B 2260/023* (2013.01); *B32B 2260/046* (2013.01); *B32B 2262/02* (2013.01); *B32B 2262/0223* (2013.01); *B32B 2262/0253* (2013.01); *B32B 2262/0269* (2013.01); *B32B 2262/101* (2013.01); *B32B 2262/103* (2013.01); *B32B 2262/105* (2013.01); *B32B 2262/106* (2013.01); *B32B 2270/00* (2013.01)

(58) Field of Classification Search
CPC .. G01N 29/069; G01N 29/30; B29D 99/0003; B29D 23/00; C08J 5/24; B29L 2031/601; B32B 3/20; B32B 5/26; B32B 7/04; B32B 27/08; B32B 27/26; B32B 27/28; B32B 27/281; B32B 27/286; B32B 27/288; B32B 27/30; B32B 27/34; B32B 27/36; B32B 27/38; B32B 27/42; B32B 3/28; B32B 7/05; B32B 2260/023; B32B 2260/046; B32B 2262/02; B32B 2262/0223; B32B 2262/0253; B32B 2262/0269; B32B 2262/101; B32B 2262/103; B32B 2262/105; B32B 2262/106; B32B 2270/00

See application file for complete search history.

(56) References Cited

U.S. PATENT DOCUMENTS

2010/0009124 A1 1/2010 Robins et al.
2011/0084428 A1 4/2011 Wade et al.

FOREIGN PATENT DOCUMENTS

| EP | 1011963 A1 | 6/2000 |
|---|---|---|
| JP | S61-265565 A | 11/1986 |
| JP | S62-39224 A | 2/1987 |
| JP | H01-313660 A | 12/1989 |
| JP | H08-52812 A | 2/1996 |
| JP | H10-227773 A | 8/1998 |

OTHER PUBLICATIONS

PCT/IB/373, "International Preliminary Report on Patentability for International Application No. PCT/JP2015/080835," dated May 2, 2017.
PCT/ISA/237, "Written Opinion of the International Searching Authority for International Application No. PCT/JP2015/080835," dated Feb. 2, 2016.
PCT/IB/326, "Notification Concerning Transmittal of International Preliminary Report on Patentability for International Application No. PCT/JP2015/080835," dated May 11, 2017.
PCT, "International Search Report for International Application No. PCT/JP2015/080835" dated Feb. 2, 2016.
Notification of Reason for Refusal, Corresponding Japanese Application No. 2014-221741, dated Mar. 31, 2015.
Decision to Grant a Patent, corresponding Japanese Application No. 2014-221741, dated Sep. 6, 2015.
Europe Patent Office, "Search Report for European Patent Application No. 15855250.5," dated Apr. 9, 2018.
"Coefficient of Thermal Expansion for Various Materials at Different Temperatures Contents," Technical Report TR-18 (Rev. F), Bal Seal Engineering, Jun. 24, 2004, p. 1-6.

ARTIFICIAL DEFECT MATERIAL AND MANUFACTURING METHOD OF FRP STRUCTURE

TECHNICAL FIELD

The present invention relates to an artificial defect material which is used for calibration of an ultrasonic test carried out after shaping of an FRP (fiber reinforced plastics) structure, and a method of manufacturing an FRP structure.

BACKGROUND ART

In recent years, the application fields of the FRP structure are expanding in the industrial products. As the merits of the FRP structure, a point of reducing the number of parts and the number of assemble steps and a point of lightening of a structure can be given.

In the FRP structure, a request for the reliability to strength is high, too. Therefore, it is important to carry out a non-destructive inspection to the FRP structure after shaping and to correctly measure the existence or non-existence of any defect. When the non-destructive inspection is carried out, a standard test piece having an artificial defect formed is necessary, and especially, it is desirable to use a standard test piece having the defect like a defect which is possibly generated. One of the defect examples which occur in an FRP structure is demolding, and the most excellent artificial defect of the standard test piece is a space (regardless of existence or non-existence of gas). The space of this artificial defect blocks off supersonic communication in the ultrasonic test in case of a transmission method, and efficiently reflects the supersonic wave in case of a reflection method.

Conventionally, as a structure of the artificial defect material and a manufacturing method, Patent Literature 1 (JP H10-227773A) describes the artificial defect material in which glass minute hollow spheres having the spherical diameter of 30-150 μm are uniformly distributed in a combination base material made of silicone rubber having the thickness 0.1-0.3 mm.

The glass minute hollow sphere in Patent Literature 1 (JP H10-227773A) has a gas therein. Because the silicone rubber which covers the glass sphere has a comparatively good supersonic characteristic, the excellent supersonic characteristics can be obtained in the supersonic test of the transmission method and the reflecting method.

In para. [0006] of Patent Literature 1 (JP H10-227773A), it is described to burry a polytetrafluoroethylene film which has the acoustic impedance different from the material, in the artificial defect material.

Also, when the FRP structure is conventionally to be shaped as a unitary body, the positions where the space should be formed are present often between the layers of fiber reinforcing base material like a corrugate structure. When the FRP structure having an interlayer space should be shaped, there are problems of how to apply a pressure in shaping and a combination of a jig and a core.

Conventionally, as a method of forming a space between the layers of the FRP structure, Patent Literature 2 (JP H08-52812A) discloses a method of manufacturing a composite material shaping body in which a composite material prepreg is arranged in an outer mold, a mandrel jig sealed with an outer skin material and filled with silicon oil (a high expansion material) is installed into the interlayer space, and silicon oil expands through heating. In this manufacturing method, by the expansion of silicon oil, the composite material prepreg is pressure shaped from it inside.

CITATION LIST

[Patent Literature 1] JP H10-227773A
[Patent Literature 2] JP H08-52812A

In the artificial defect material described in Patent Literature 1, a space inside the glass minute hollow sphere is used in place of a defect part. Since the space inside the glass minute hollow sphere is distributed in the inside of the artificial defect material, the shape is different from the continued space formed due to demolding in the FRP structure. Therefore, when being used as the standard test piece for the ultrasonic test of the FRP structure, there are inconvenient points such as difference of obtained corrugation shape, increase of noise, and necessity of calibration.

The artificial defect material described in Patent Literature 1 is added to contain the glass minute hollow spheres of about 30-60%. This is because a possibility increases that the attenuation rate increase in the transmission method of the artificial defect material or the reflectivity decreases in the reflection method, when the content of the glass minute hollow spheres falls below 30%, as described in para. [0031], [0032] and so on Patent Literature 1. Also, there is another problem that the strength of the artificial defect material lack, when the content of the glass minute hollow spheres exceed 60%.

As described in para. [0006] of Patent Literature 1, In case of the artificial defect material using a polytetrafluoroethylene film, there are problems that the film is stuck to the composite material without releasing from the composite material, so as not to function as the artificial defect material at all, or, the film is partially delaminated, so that the defect size is not clear and the reliability and stability as the standard test piece are low. When the signal-to-noise ratio of a signal obtained from the standard test piece is low, many man-days became necessary to the ultrasonic test, such as the secondary inspection is required in which the focus of the supersonic wave is changed.

Also, in the method of manufacturing the composite material shaping body described in Patent Literature 2, the composite material prepreg is pressure shaped (hollow shaping) from inside of the interlayer space by using the mandrel jig formed of a material inferior to the form keeping property such as silicon oil, in the interlayer space of the FRP structure. For this reason, the precision of inner shape of the interlayer space and the precision of thickness in a local part could not be prescribed in the FRP structure. Also, the inner shape of the interlayer space could not be formed to have a complicated shape through once shaping.

SUMMARY OF THE INVENTION

An object of the present invention is to provide a manufacturing method of an FRP structure in which the interlayer space is shaped in high precision, the FRP structure and the FRP structure available as an artificial defect material.

The artificial defect material according to the present invention includes a plurality of layers of fiber reinforcing base material, a matrix resin and a heat-resistant high-linear-expansion material. The matrix resin unifies the plurality of layers of fiber reinforcing base material to form an FRP structure. Generally, there are a case of preparing the fiber reinforcing base material and the matrix resin individually to form the FRP structure, and a case of preparing a prepreg material in which the matrix resin is impregnated into the fiber reinforcing base material previously to form the FRP structure. Also, according to need, an adhesive material is applied to the layers of the fiber reinforcing base material or prepreg material. The heat-resistant high-linear-expansion material is arranged in at least one interlayer of the fiber reinforcing base material (the prepreg material). The heat-resistant high-linear-expansion material has the shape keeping property and the heat resistance to endure the shaping temperature of the FRP structure, and has a linear expansion coefficient larger than the linear expansion coefficient of the FRP structure by a predetermined value or more. The heat-resistant high-linear-expansion material thermally expand to shape a predetermined shape between the layers of fiber reinforcing base material (the prepreg material), when the temperature increases to the shaping temperature higher than the room temperature in case of shaping the FRP structure. In the room temperature after shaping the FRP structure, a space is formed between the heat-resistant high-linear-expansion material and the layers of fiber reinforcing base material (prepreg material) due to a shrinkage difference through the thermal shrinkage.

The method of manufacturing the artificial defect material according to the present invention has arranging layers of fiber reinforcing base material; arranging the heat-resistant high-linear-expansion material between at least one pair of layers of fiber reinforcing base material; impregnating a matrix resin into the fiber reinforcing base material; increasing a temperature of the fiber reinforcing base material, the heat-resistant high-linear-expansion material and the matrix resin to a shaping temperature which is higher than the room temperature to make the heat-resistant high-linear-expansion material thermally expand to form a predetermined shape between the layers of fiber reinforcing base material; and lowering the FRP structure to the room temperature to make the heat-resistant high-linear-expansion material carry out thermal shrinkage to form the space between the heat-resistant high-linear-expansion material and the layer of fiber reinforcing base material due to the shrinkage difference.

A method of manufacturing the artificial defect material by using a prepreg material according to the present invention includes arranging a heat-resistant high-linear-expansion material in at least one pair of layers of prepreg material, increasing a temperature of the prepreg material and the heat-resistant high-linear-expansion material to a shaping temperature which is higher than the room temperature to make the heat-resistant high-linear-expansion material thermally expand to form a predetermined shape between the layers of prepreg material; and lowering the FRP structure to the room temperature to make the heat-resistant high-linear-expansion material carry out thermal shrinkage to form the space between the heat-resistant high-linear-expansion material and the layer of prepreg material due to the shrinkage difference.

A method of manufacturing an FRP structure according to the present invention includes arranging layers of fiber reinforcing base material; arranging a heat-resistant high-linear-expansion material in at least one pair of layers of fiber reinforcing base material; impregnating a matrix resin into the fiber reinforcing base material; increasing a temperature of the prepreg material, the heat-resistant high-linear-expansion material and the matrix resin to a shaping temperature which is higher than the room temperature to make the heat-resistant high-linear-expansion material thermally expand to form a predetermined shape between the layers of prepreg material; lowering the FRP structure to the room temperature to make the heat-resistant high-linear-expansion material carry out thermal shrinkage to form the space between the heat-resistant high-linear-expansion material and the layer of prepreg material due to the shrinkage difference; and removing the heat-resistant high-linear-expansion material from the interlayer of the fiber reinforcing base material.

The FRP structure includes a plurality of layers of fiber reinforcing base material and a matrix resin. The matrix resin unifies the plurality of layer of fiber reinforcing base material into an FRP structure. There is an interlayer space formed by using the heat-resistant high-linear-expansion material in at least one pair of layers of fiber reinforcing base material. The heat-resistant high-linear-expansion material has the shape keeping property and the heat resistance so as to endure a shaping temperature of the FRP structure. The heat-resistant high-linear-expansion material has a linear expansion coefficient larger than that of the FRP structure by a predetermined value or more. Also, the Shore hardness of the heat-resistant high-linear-expansion material is within a range of A20 to A70.

A method of manufacturing an FRP structure by using a prepreg material according to the present invention includes arranging layers of prepreg material; arranging a heat-resistant high-linear-expansion material in at least one pair of layers of prepreg material; increasing the heat-resistant high-linear-expansion material and the prepreg material to a shaping temperature which is higher than the room temperature to make the heat-resistant high-linear-expansion material thermally expand to form an interlayer space having a predetermined shape between the layers of prepreg material; lowering the temperature of the FRP structure to the room temperature to make the heat-resistant high-linear-expansion material thermally shrink to form the space between the heat-resistant high-linear-expansion material and the layer of prepreg material due to a shrinkage difference; and removing the heat-resistant high-linear-expansion material from the interlayer of the prepreg material.

An FRP structure has an interlayer space formed by using the heat-resistant high-linear-expansion material between two of a plurality of layers of prepreg material. The heat-resistant high-linear-expansion material has the shape keeping property and the heat resistance to endure the shaping temperature of the FRP structure. The heat-resistant high-linear-expansion material has a linear expansion coefficient larger than that of the FRP structure by a predetermined value or more. Also, the Shore hardness of the heat-resistant high-linear-expansion material is within a range of A20 to A70.

The arranging step may include arrange a plurality of heat-resistant high-linear-expansion materials in a plurality of interlayers of the fiber reinforcing base material or the prepreg material.

The heat-resistant high-linear-expansion material is formed of a material selected from the group consisting of silicone rubber, silicone resin, fluororubber, natural rubber, butadiene rubber, styrene rubber, butyl rubber, nitrile rubber, ethylene propylene rubber, chlorosulfonated polyethylene rubber and urethane rubber.

The mold releasing material of a silicon system or a fluorine system is applied to the surface of the heat-resistant high-linear-expansion material.

By using the artificial defect material and the manufacturing method of the FRP structure according to the present invention, the FRP structure which has a space in an interlayer of the fiber reinforcing base material can be shaped in high precision.

DESCRIPTION OF THE EMBODIMENTS

Embodiments of a method of manufacturing an artificial defect material and an FRP structure according to the present invention will be described below with reference to the attached drawings.

First Embodiment

Figure 1:
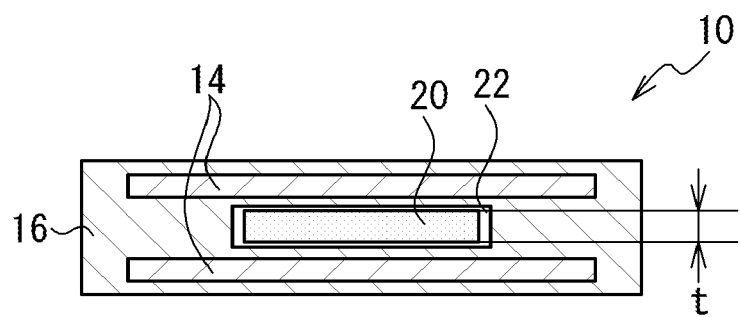
FIG. 1 is a sectional view of an artificial defect material (a standard test piece) of the present invention.

FIG. 1 is a sectional view of an artificial defect material 10 completed through cooling (a standard test piece).

Referring to FIG. 1, the artificial defect material 10 includes a fiber reinforcing base material 14, a matrix resin 16, a heat-resistant high-linear-expansion material (an intermediate structure) 20, a space 22 formed based on a shrinkage difference.

The artificial defect material 10 can be used as a part of the standard test piece for calibration when an ultrasonic test is carried out after an FRP structure (a sample) is shaped. The artificial defect material 10 is an FRP structure in which stacked layers of the fiber reinforcing base material 14 are adhered with the matrix resin 16 and then cured, and is possible to use as a part to simulate demolding.

The heat-resistant high-linear-expansion material (intermediate structure) 20 is a material in which thermal expansion and thermal shrinkage are carried out based on temperature increasing to the curing temperature of the matrix resin 16 upon a thermo shaping and lowering to the room temperature after the thermo shaping. The heat-resistant high-linear-expansion material 20 is selected so that a linear expansion coefficient of the heat-resistant high-linear-expansion material 20 is more than that of the FRP structure.

Figure 4:
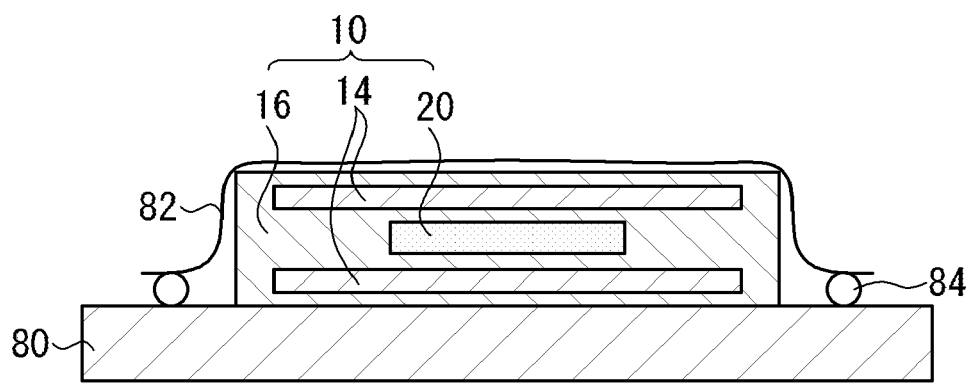
FIG. 4 is a sectional view showing the artificial defect material in the thermo shaping.

In case of the thermo shaping, the volume of the heat-resistant high-linear-expansion material 20 increases while keeping the predetermined shape without changing the shape, as shown in FIG. 4, though the heat-resistant high-linear-expansion material 20 thermally expands. The heat-resistant high-linear-expansion material 20 functions as a core to form a predetermined shape inside the FRP structure of the artificial defect material 10.

As shown in FIG. 1, the thermal shrinkage of the heat-resistant high-linear-expansion material 20 occurs during the cooling, to decrease the volume. In this case, a space 22 is formed due to a shrinkage difference between the predetermined shape formed inside the FRP structure for the artificial defect material 10 and the heat-resistant high-linear-expansion material 20 that has shrunk thermally. The space 22 can be used as an artificial defect of the standard test piece in the ultrasonic test.

The heat-resistant high-linear-expansion material 20 is a solid material with, for example, 10-80 μm in thick, and the width and the length can be appropriately set according to a defect in the sample. The heat-resistant high-linear-expansion material 20 has the linear expansion coefficient larger than the linear expansion coefficient of the FRP structure, desirably, by $100 \times 10^{-6}$ (1/° C.) or more, more desirably, by $150 \times 10^{-6}$ (1/° C.) or more, and further more desirably, by $200 \times 10^{-6}$ (1/° C.) or more. Also, the heat-resistant high-linear-expansion material 20 needs to have heat resistance to endure the curing temperature (130-500° C. according to a kind of resin) of the matrix resin 16 in the thermo shaping shown in FIG. 4.

It is supposed that the linear expansion coefficient Δ1 of the FRP structure is $30 \times 10^{-6}$ (1/° C.), the linear expansion coefficient Δ2 of the heat-resistant high-linear-expansion material 20 is $230 \times 10^{-6}$ (1/° C.), the temperature in case of thermo shaping is 180° C., the room temperature after cooling is 15° C., the temperature difference ΔT is 165° C., and the thickness t of the heat-resistant high-linear-expansion material 20 is 30 μm. In this case, the size of the space 22 formed due to the shrinkage difference in the thickness direction.

The size H of the space 22 formed due to the shrinkage difference in this case is $(\Delta 1 - \Delta 12) \times \Delta T \times t \approx -1$ μm. This 1-μm space (the space 22 formed due to the shrinkage difference) is a space produced between the heat-resistant high-linear-expansion material 20 and the layer of fiber reinforcing base material 14 or the matrix resin 16, and is equivalent to the space due to the interlayer demolding occurring actually in the FRP structure (sample) of an actual product. Note that the size H of the space 22 formed due to the shrinkage difference is desirably equal to or more than 0.1 μm. It is more desirable that the size H of the space 22 formed due to the shrinkage difference is equal to or more than 1 μm.

The space 22 formed due to the shrinkage difference strongly reflects the supersonic wave used in the ultrasonic test. Also, since the thickness of the heat-resistant high-linear-expansion material 20 can be made thin, the artificial defect material 10 can be formed by using the shape and the manufacturing method like the sample. Therefore, since there are few constraints about the artificial defect material 10, the standard test piece imitating the FRP structure (the sample) of many kinds can be easily manufactured.

By using the artificial defect material 10 shown in FIG. 1, a noise component on the calibration of the ultrasonic test can be reduced, and the number of inspection steps can be reduced by omitting a secondary inspection in the ultrasonic test of the FRP structure (the sample).

By using a material having a large linear expansion coefficient as the heat-resistant high-linear-expansion material 20, the heat-resistant high-linear-expansion material 20 thermally shrinks through the cooling of the FRP structure and becomes easy to be pulled out from the FRP structure. Thus, the demolding between the heat-resistant high-linear-expansion material 20 and the FRP structure is made surer, and it is possible to provide a high-quality standard test piece having the space formed by the uniform shrinkage difference.

Also, in the manufacturing the artificial defect material 10, a mold releasing process is carried out of applying a mold releasing material on the surface of the heat-resistant high-linear-expansion material 20, before the heat-resistant high-linear-expansion material 20 is arranged between the layers of fiber reinforcing base material 14. Thus, it is possible to promote the demolding of the heat-resistant high-linear-expansion material 20 in the cooling.

It is desirable to use silicone rubber or silicone resin which is excellent in the demolding, as the material of the heat-resistant high-linear-expansion material 20. Also, when a high heat resistance is necessary, fluororubber (a material having the linear expansion coefficient larger than fluorine resin) can be used. Also, the material selected from the group consisting of natural rubber, butadiene rubber, styrene rubber, butyl rubber, nitrile rubber, ethylene propylene rubber, and chlorosulfonated polyethylene rubber can be used as the material having intermediate heat resistance. Also, when the heat resistance is unnecessary, a material such as urethane rubber can be used. Also, the material having the Shore hardness in a range of A20 to A70 can be used.

It is desirable to select the material of the heat-resistant high-linear-expansion material 20, in consideration of a price, a shaping temperature, a chemical resistance to the mold releasing material to be used, the size of the space formed due to a required shrinkage difference and so on (the difference from the linear expansion coefficient of the FRP structure).

Fluorine system compounds and silicon system compounds can be used for the mold releasing material.

Figure 2:
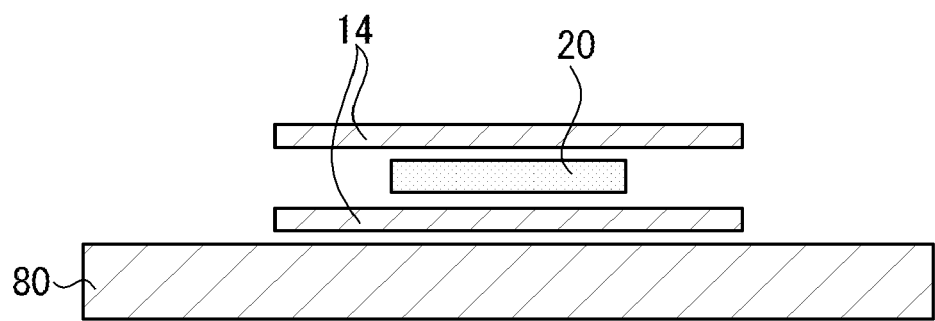
FIG. 2 is a sectional view showing the condition that a fiber reinforcing base material and a heat-resistant high-linear-expansion material are arranged and stacked on a jig.
Figure 3:
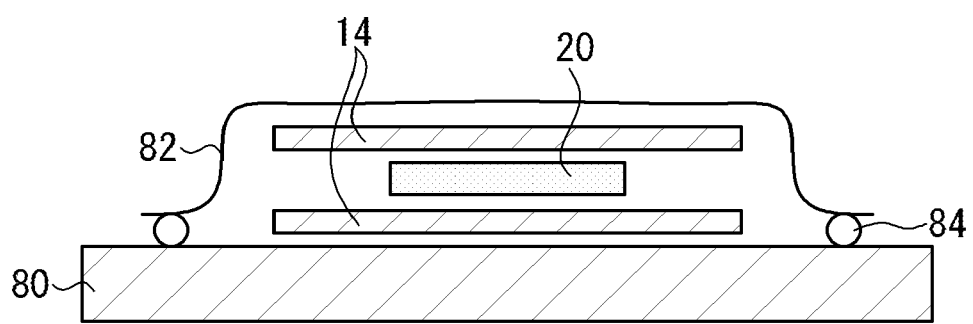
FIG. 3 is a sectional view showing the condition that the fiber reinforcing base material and the heat-resistant high-linear-expansion material are covered with a bag to secure the airtightness between the bag and the jig.

Next, the manufacturing method of the artificial defect material 10 shown in FIG. 1 (of the heat curing type) will be described. FIG. 2 is a sectional view showing the state that layers of the fiber reinforcing base material 14 and the heat-resistant high-linear-expansion material 20 are stacked on a jig 80. FIG. 3 is a sectional view showing the state that the fiber reinforcing base material 14 and the heat-resistant high-linear-expansion material 20 are covered with a bag 82 to secure airtightness between the bag 82 and the jig 80. FIG. 4 is a sectional view of the artificial defect material 10 in thermo shaping.

The method of manufacturing the artificial defect material 10 includes:

Step 1: arranging the layers of fiber reinforcing base material 14;

Step 2: arranging the heat-resistant high-linear-expansion material 20 between the layers of fiber reinforcing base material 14;

Step 3: covering the fiber reinforcing base material 14 with the bag 82;

Step 4: evacuating the inside of the bag 82 in which the fiber reinforcing base material 14 is arranged;

Step 5: injecting the matrix resin 16 into the inside of the bag 82 in which the fiber reinforcing base material 14 is arranged;

Step 6: raising the temperature of the fiber reinforcing base material 14, the heat-resistant high-linear-expansion material 20 and the matrix resin 16 to a thermo shaping temperature which is higher than the room temperature, to thermally shape the FRP structure; and Step 7: lowering the material temperature to the room temperature after shaping of the FRP structure.

Step 1:

Referring to FIG. 2, when the artificial defect material 10 is to be shaped, the layers of fiber reinforcing base material 14 are arranged on the jig 80 having a predetermined shape. Metal, the FRP structure, a gypsum, and other material can be used as the material of jig 80 which is selected in consideration of the heat resistance of the jig material and the curing temperature. Also, it is desirable that the material having the linear expansion coefficient near that of the FRP structure is used for the jig 80.

Step 2:

The mold releasing material is applied to the surface of the heat-resistant high-linear-expansion material 20 according to need. Then, the heat-resistant high-linear-expansion material 20 with a predetermined size is arranges in a predetermined position between at least one pair of layers of fiber reinforcing base material 14.

Step 3:

Referring to FIG. 3, the fiber reinforcing base material 14 and the heat-resistant high-linear-expansion material 20 are covered with auxiliary materials such as sealant 84 and the bag 82 so as to secure the airtightness between bag 82 and the jig 80. Note that although the sealant 84 and the bag 82 are shown as the auxiliary materials in the embodiment shown in FIG. 3, other auxiliary materials such as a peel ply and a breather cloth may be arranged according to need.

Step 4:

The space which is surrounded by the jig 80 and the bag 82 and in which the fiber reinforcing base material 14 is arranged is evacuated so as to apply a pushing pressure to the fiber reinforcing base material 14 by using the atmosphere pressure.

Step 5:

The matrix resin 16 is injected into the vacuumed space such that the matrix resin 16 impregnates into the layers of fiber reinforcing base material 14 and fiber reinforcing base material 14.

Step 6:

When the matrix resin 16 of a thermosetting type is used, the fiber reinforcing base material 14, the heat-resistant high-linear-expansion material 20 and the matrix resin 16 are heated to a thermo shaping temperature, and the matrix resin 16 is cured for a predetermined time, to unify a plurality of layers of fiber reinforcing base material 14 and the matrix resin. The heat-resistant high-linear-expansion material 20 arranged between the layers of fiber reinforcing base material 14 thermally expands through the temperature increasing, to function as a core in the general resin shaping, so that the shape of the artificial defect material is formed (reference to FIG. 4). For example, the curing time by the temperature increasing is 2-3 hours.

Step 7:

When the predetermined curing time elapses so that the matrix resin 16 has been cured, the temperature of the FRP structure is decreased to the room temperature so as to form the artificial defect material 10 of the FRP structure. At this time, a space is formed due to the shrinkage difference as a result of a difference between the heat-resistant high-linear-expansion material 20 and the FRP structure in the linear expansion coefficient. After that, when the bag 82 is removed, the artificial defect material 10 shown in FIG. 1 is obtained.

Note that a trimming process may be added according to need, such that a part of the FRP structure (the standard test piece) is cut to take out the heat-resistant high-linear-expansion material 20 from the FRP structure (the standard test piece). After shaping of the FRP structure (the standard test piece), the standard test piece which does not contain the heat-resistant high-linear-expansion material 20 can be manufactured, by taking out the heat-resistant high-linear-expansion material 20 from the FRP structure (the standard test piece).

By using the heat-resistant high-linear-expansion material 20 having a large linear expansion coefficient and excellent in demolding, the space can be formed between the FRP structure and the heat-resistant high-linear-expansion material 20 after the cooling. Also, it becomes easy to pull out or remove the heat-resistant high-linear-expansion material 20 from the FRP structure after cooling, by using the heat-resistant high-linear-expansion material 20 having a large linear expansion coefficient and excellent in demolding.

As the material of fiber reinforcing base material 14, carbon fiber, glass fiber, organic fiber such as aramid fiber, polyparaphenylene benzobisoxazole fiber, phenol fiber, polyethylene fiber, and polyvinyl alcohol fiber, metal fiber, and ceramic fiber, or a combinations of them may be used. Also, a prepreg material may be used.

Also, as the matrix resin 16, the thermoplastic resin or the thermosetting resin may be used. It is desirable to use the thermosetting resin in the present situation from the viewpoint of the shapability and dynamic characteristics. For example, as the thermosetting resin, various types of resin such as epoxy resin, phenol resin, vinyl ester resin, unsaturated polyester resin, cyanate ester resin, bismaleimide resin, and benzoxazine resin may be used. To cure, a curing material, a curing accelerator, a polymerization initiator, a catalyst and so on are added. Moreover, the resin added with an elastomer, rubber and so on can be used. Note that it is desirable that a mold releasing material and resin diffusion media are arranged beforehand on the side of the fiber reinforcing base material 14 of the jig 80 and the bag.

Although in the above-mentioned embodiment, the resin of the thermosetting type is used as matrix resin 16, the artificial defect material 10 (the standard test piece) using a thermoplastic type resin can be shaped. As the thermoplastic resin, for example, PPS (polyphenylene sulfide), PEEK (polyether etherketone), PEKK (polyether ketoneketone), PEK (polyether ketone), PI (polyimide), PEI (polyether imide), PA (nylon polyamide), and so on can be used.

When the thermoplastic type resin is used as the matrix resin 16, the matrix resin 16 softened under a high temperature impregnated into the layers of fiber reinforcing base material 14 and fiber reinforcing base material 14, after the heat-resistant high-linear-expansion material 20 with a predetermined size is arranged in a predetermined position of the fiber reinforcing base material 14. At this time, the heat-resistant high-linear-expansion material 20 thermally expands through the temperature increasing, to form the shape of the artificial defect. After that, when the temperature of the FRP structure (the standard test piece) is lowered to the room temperature, a space is formed due to the shrinkage difference between the FRP structure (the standard test piece) and the heat-resistant high-linear-expansion material 20 as a result of the difference between the FRP structure (the standard test piece) and the heat-resistant high-linear-expansion material 20 in the linear expansion coefficient. Thus, the artificial defect material 10 shown in FIG. 1 is obtained. Also, the artificial defect material 10 can be formed by using the thermoplastic prepreg material in place of the fiber reinforcing base material 14 and the matrix resin 16.

Figure 5:
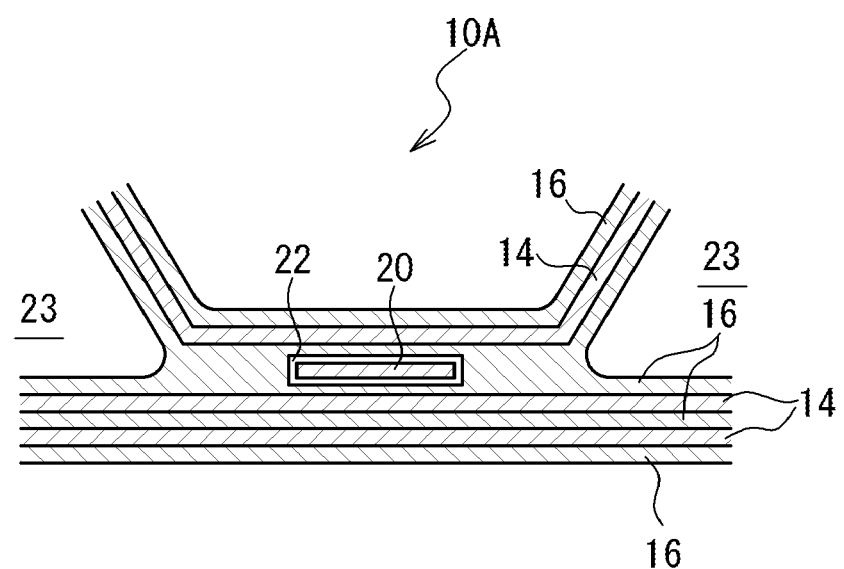
FIG. 5 is a diagram showing a structural example of the artificial defect material that has a plurality of layers of fiber reinforcing base material.

Next, referring to FIG. 5, another configuration example of the artificial defect material will be described. FIG. 5 is a diagram showing a configuration example of the artificial defect material in which the fiber reinforcing base material 14 is a multiple layer structure and a space 23 is formed between the layers of fiber reinforcing base material 14. Note that an identical reference numeral is used for a part having the same function as the part shown in FIG. 1, and the description of it is omitted.

The shape and configuration of the artificial defect material are not limited to the artificial defect material 10 shown in FIG. 1, and may be appropriately set according to the shape and configuration of the FRP structure as a sample. For example, in the artificial defect material 10A shown in FIG. 5, the fiber reinforcing base material 14 is shown to have 3 layers but and is shown but may have more than tens of layers. Also, the space 22 (the artificial defect) formed due to the shrinkage difference is possible to be arrange at an appropriate position according to need. Moreover, the position of the space 22 is not limited to a position between two layers of fiber reinforcing base material 14 and a layer of an adhesive material may be used in place of one layer of the fiber reinforcing base material 14.

Second Embodiment

Figure 6:
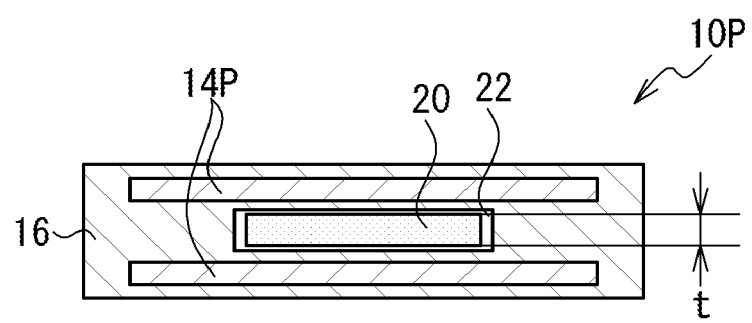
FIG. 6 is a sectional view of the artificial defect material (standard test piece) using a prepreg material after cooling.
Figure 7:
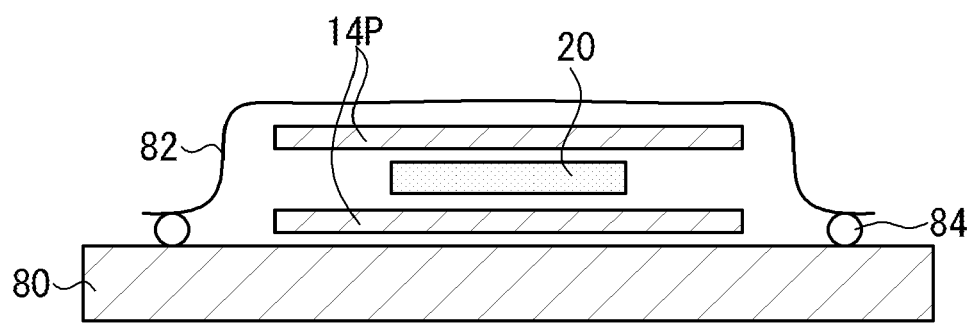
FIG. 7 is a sectional view showing the condition that the prepreg material and the heat-resistant high-linear-expansion material are arranged and stacked on the jig to secure airtightness between the bag and the jig.
Figure 8:
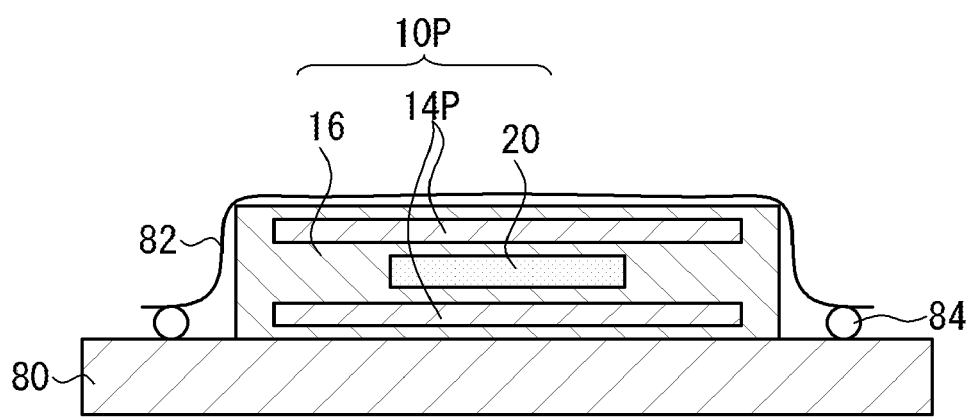
FIG. 8 is a sectional view of the artificial defect material in the thermo shaping.

Next, the artificial defect material 10P using a prepreg material 14P (a base material in which the matrix resin 16 has been impregnated into the fiber reinforcing base material) will be described with reference to FIG. 6 to FIG. 8. FIG. 6 is a sectional view of the artificial defect material 10P (the standard test piece) completed after cooling. FIG. 7 is a sectional view showing the state in which the layers of prepreg material 14P and heat-resistant high-linear-expansion material 20 are arranged on the jig 80, and covered with the bag 82, to secure airtightness between the bag 82 and the jig 80. FIG. 8 is a sectional view of the artificial defect material 10P in the thermo shaping.

Referring to FIG. 6, the artificial defect material 10P includes the prepreg material 14P, the heat-resistant high-linear-expansion material 20 and the space formed due the shrinkage difference. Although not shown in FIG. 6, the space formed due the shrinkage difference is not limited to the formation between two layers of fiber reinforcing base material 14, and one of the two layers may be formed of an adhesive material, according to the shape and configuration of the FRP structure as a sample.

The artificial defect material 10P is the standard test piece used for the calibration when an ultrasonic test is carried out, after shaping the FRP structure (the sample) as a product. The artificial defect material 10P is the standard test piece of the FRP structure in which the layers of prepreg material 14P are unified and cured.

The heat-resistant high-linear-expansion material 20 thermally expands and thermally shrinks according to the temperature difference between the curing temperature of the prepreg material 14P in the thermo shaping and the room temperature after cooling. The heat-resistant high-linear-expansion material 20 is selected so that the linear expansion coefficient of the heat-resistant high-linear-expansion material 20 is greater than the linear expansion coefficient of the FRP structure.

In case of thermo shaping, the heat-resistant high-linear-expansion material 20 thermally expands to increase the volume while maintaining a constant form, as shown in FIG. 8. The heat-resistant high-linear-expansion material 20 functions as the core to form a predetermined shape inside the FRP structure as the artificial defect material 10P.

After the cooling, as shown in FIG. 6, the heat-resistant high-linear-expansion material 20 thermally shrinks to decrease the volume. At this time, the space is formed due to the shrinkage difference between the heat-resistant high-linear-expansion materials 20 having thermally shrunk and the predetermined shape formed inside the FRP structure as the artificial defect material 10P. The space can be used as the artificial defect when used as the standard test piece for the ultrasonic test.

The material and size used in the first embodiment can be used for the heat-resistant high-linear-expansion material 20, the mold releasing material, the heat-resistant high-linear-expansion material 20, the jig 80, the bag 82, the sealant 84 and son.

Next, the method of manufacturing the artificial defect material 10P shown in FIG. 6 (the thermosetting type) will be described.

The method of manufacturing the artificial defect material 10P (the thermosetting type) includes:

Step 11: arranging the layers of prepreg material 14P;

Step 12: arranging the heat-resistant high-linear-expansion material (the intermediate structure) 20 between the layers of prepreg material 14P;

Step 13: covering the prepreg material with the bag 82;

Step 14: evacuating the inside of the bag 8 in which the prepreg material 14P is arranged;

Step 15: increasing the temperature of the prepreg material 14P and the heat-resistant high-linear-expansion material 20 to a higher temperature than the room temperature, to carry out the thermo shaping the FRP structure; and Step 16: lowering the temperature to the room temperature after thermo shaping of the FRP structure.

Step 11:

Referring to FIG. 7, the layers of prepreg material 14P are arranged on the jig 80 having a predetermined shape, when the artificial defect material 10P should be thermo-shaped.

Step 12:

The mold releasing material is applied to the surface of the heat-resistant high-linear-expansion material 20 according to need. The heat-resistant high-linear-expansion material (the intermediate structure) 20 with a predetermined size is arranged in a predetermined position between the layers of the prepreg material 14P.

Step 13:

Referring to FIG. 7, the prepreg material 14P and the heat-resistant high-linear-expansion material 20 are covered with the auxiliary materials such as the sealant 84 and the bag 82 to secure the airtightness between the bag 82 and the jig 80. Note that although the sealant sealant 84 and the bag 82 are shown as the auxiliary materials in the embodiment shown in FIG. 7, other auxiliary materials such as a peel ply and breather cloth may be arranged according to need.

Step 14:

An internal portion which is surrounded by the jig 80 and the bag 82 and in which the prepreg material 14P is arranged is evacuated to a vacuum so as to apply pushing force to the prepreg material 14P by using the atmosphere pressure.

Step 15:

When the matrix resin 16 is of the thermosetting type, the prepreg material 14P, the heat-resistant high-linear-expansion material 20 and the matrix resin 16 is heated to the thermo shaping temperature, and the prepreg material 14P and the matrix resin 16 are cured for a predetermined time to unify the layers of prepreg material 14P. The heat-resistant high-linear-expansion material 20 arranged between the layers of prepreg material 14P thermally expands by the temperature increasing to function as a core in general resin shaping, resulting in forming the shape of an artificial defect (reference to FIG. 8).

Step 16:

When a predetermined curing time elapses and the matrix resin 16 is cured, the temperature of the FRP structure is lowered to the room temperature to form the artificial defect material 10P of the FRP structure. At this time, a space is formed due to the shrinkage difference as a result of the difference between the FRP structure and the heat-resistant high-linear-expansion material 20 in the linear expansion coefficient. After that, when the bag 82 is removed, the artificial defect material 10P shown in FIG. 6 is obtained.

Third Embodiment

In the above-mentioned first embodiment, the heat-resistant high-linear-expansion material 20 is arranged between the layers of fiber reinforcing base material 14 and the heat-resistant high-linear-expansion material 20 is thermally expanded under the high shaping temperature, to function as the core in resin shaping. Thus, the shape of the artificial defect part is formed. By lowering to the room temperature after the shaping, the embodiment has been shown in which the space 22 is formed due to the shrinkage difference as the result of the difference between the FRP structure and the heat-resistant high-linear-expansion material 20 in the linear expansion coefficient.

On the other hand, in a third embodiment, the heat-resistant high-linear-expansion material 20 is arranged between the layers of fiber reinforcing base material 14 and thermally expanded under the high shaping temperature to function as the core in resin shaping. Thus, the temperature is lowered to the room temperature after the shaping, and as a result, the space 22 is formed due to the shrinkage difference as a result of the difference between the FRP structure 12 and the heat-resistant high-linear-expansion material 20 in the linear expansion coefficient, so that the heat-resistant high-linear-expansion material 20 is made easy to be pulled out.

Figure 9:
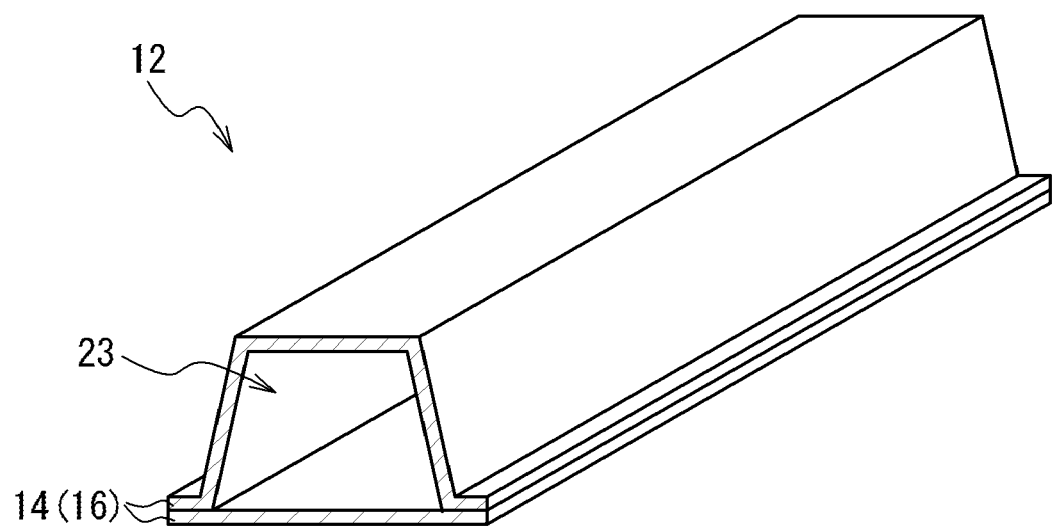
FIG. 9 is a perspective view of an outward appearance of the FRP structure having an interlayer space surrounded with two fiber reinforcing base materials after completion.

FIG. 9 is an outward appearance perspective view of the FRP structure 12 having an interlayer space 23 surrounded by two layers of fiber reinforcing base material 14 after the completion.

Referring to FIG. 9, the FRP structure 12 has the plurality of layers of fiber reinforcing base material 14, the matrix resin 16 and the interlayer space 23 surrounded by the layers of fiber reinforcing base material 14 (a space having a trapezoidal sectional shape in the embodiment shown in FIG. 9).

The FRP structure 12 is formed by unifying the stacked layers of fiber reinforcing base material 14 with the matrix resin 16 and curing them, and is a structure material such as a stringer and a mold material. Note that the interlayer space 23 can be shaped to various shapes.

Figure 10:
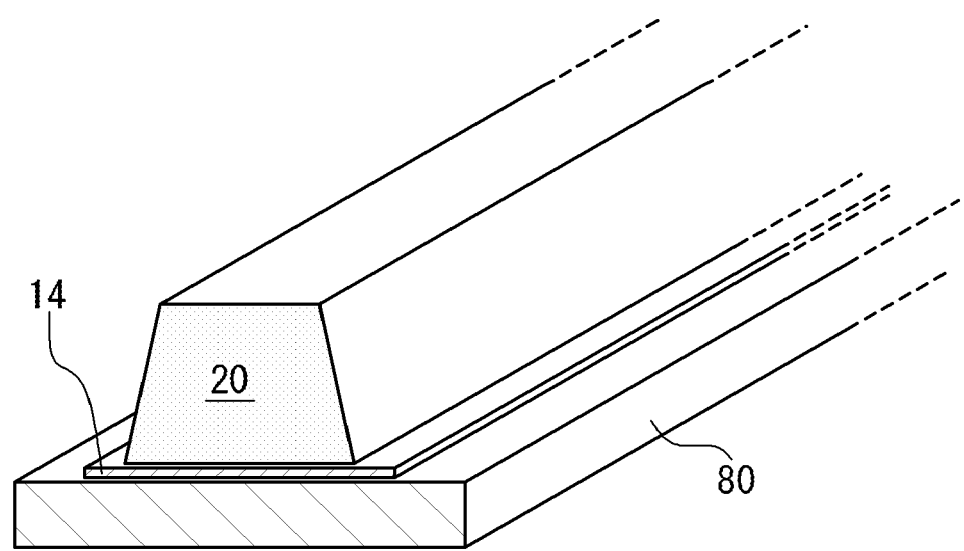
FIG. 10 is a diagram showing the condition that the fiber reinforcing base material and the heat-resistant high-linear-expansion material are arranged on the jig for shaping.
Figure 11:
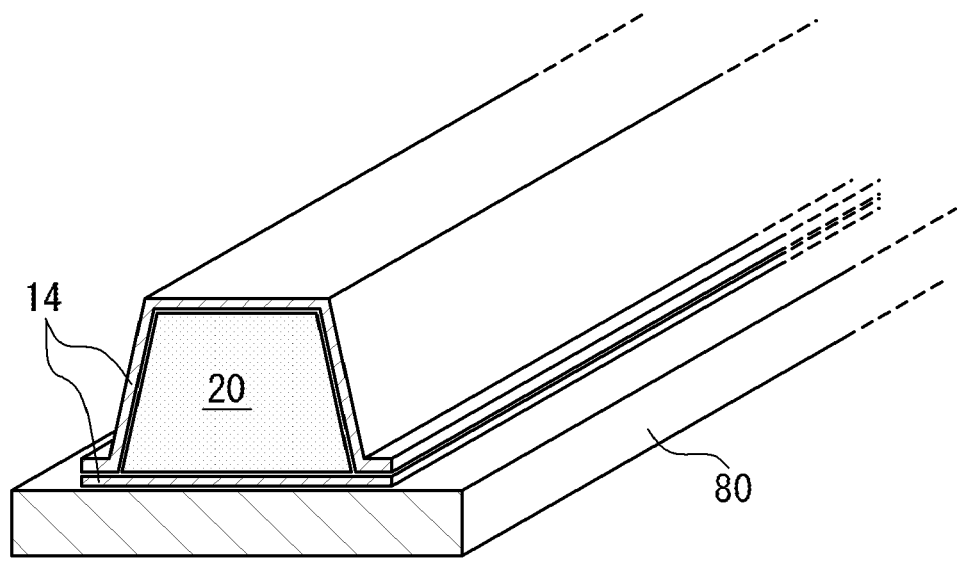
FIG. 11 is a diagram showing the condition that the fiber reinforcing base material is arranged on the heat-resistant high-linear-expansion material to surround the heat-resistant high-linear-expansion material.
Figure 12:
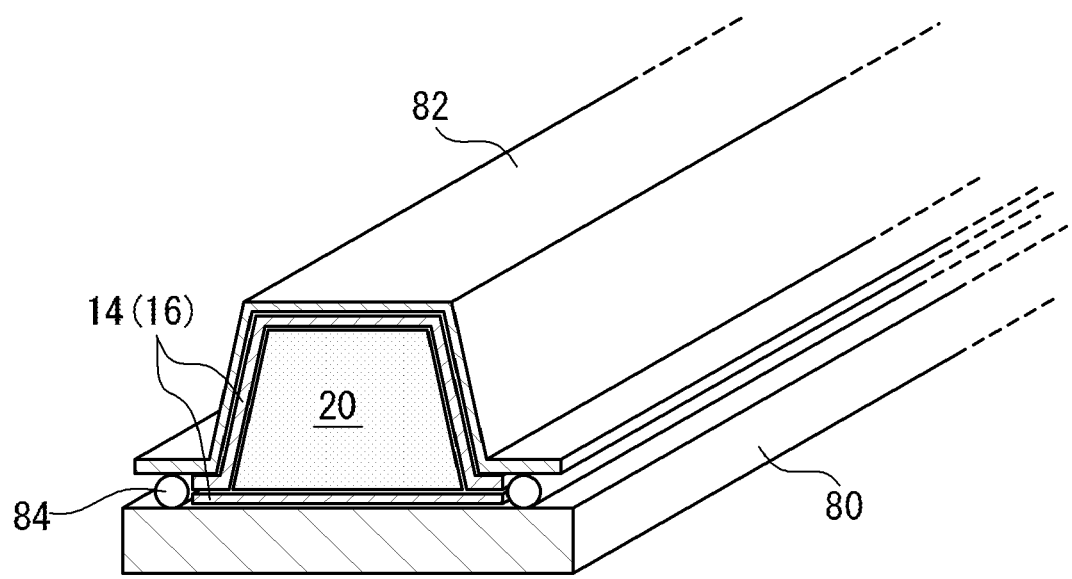
FIG. 12 is a diagram showing the condition of the thermo shaping in which the fiber reinforcing base material and the heat-resistant high-linear-expansion material are covered with the bag to secure the airtightness between the bag and the jig.
Figure 13:
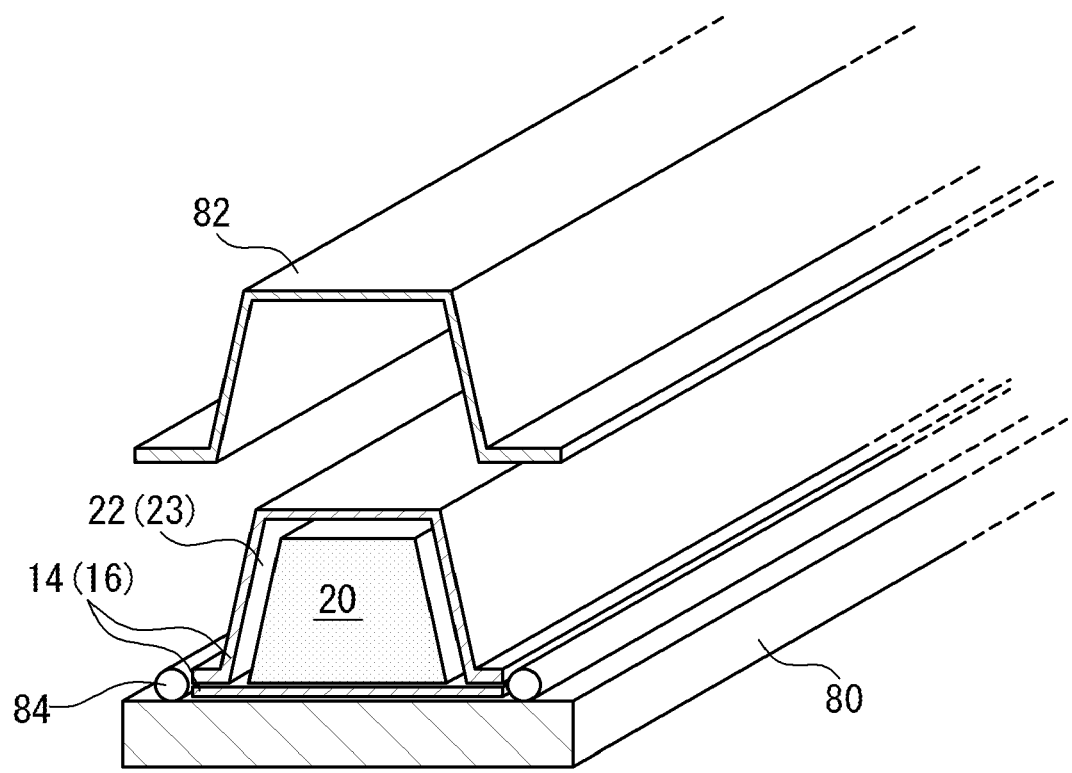
FIG. 13 is a diagram showing the condition that the bag is removed at the room temperature after shaping the FRP structure.

Next, the method of manufacturing the FRP structure 12 shown in FIG. 9 will be described with reference to FIG. 10 to FIG. 13. FIG. 10 is a diagram showing a state that the fiber reinforcing base material 14 and the heat-resistant high-linear-expansion material 20 are arranged on the jig 80 for shaping. FIG. 11 is a diagram showing a state that the fiber reinforcing base material 14 is arranged from an upper location to surround the heat-resistant high-linear-expansion material 20. FIG. 12 is a diagram showing a thermo shaping state that the fiber reinforcing base material 14 and the heat-resistant high-linear-expansion material 20 are with the bag 82 to secure the airtightness between the bag 82 and the jig 80. FIG. 13 is a diagram showing a state that the bag 82 is removed in the room temperature after the shaping of the FRP structure 12.

The manufacturing method of the FRP structure 12 shown in FIG. 9 includes:

Step 21: arranging the fiber reinforcing base material 14;

Step 22: arranging the heat-resistant high-linear-expansion material 20 between the layers of fiber reinforcing base material 14;

Step 23: covering the fiber reinforcing base material 14 with the bag 82;

Step 24: evacuating the inside of the bag 82 in which the fiber reinforcing base material 14 is arranged, to a vacuum;

Step 25: injecting the matrix resin 16 into the inside of the bag 82 in which the fiber reinforcing base material 14 is arranged;

Step 26: heating the fiber reinforcing base material 14, the heat-resistant high-linear-expansion material 20 and the matrix resin 16 to a higher shaping temperature than the room temperature to shape the FRP structure; and Step 27: lowering the temperature to the room temperature after shaping of the FRP structure 12.

Step 21:

Referring to FIG. 10, when the FRP structure 12 is to be shaped, the layers of fiber reinforcing base material 14 are stacked on the jig 80 having a predetermined shape.

Step 22:

A mold releasing material is applied to the surface of the heat-resistant high-linear-expansion material 20 according to need. The heat-resistant high-linear-expansion material 20 having a predetermined size is arranged in a predetermined position between at least one pair of layers of fiber reinforcing base material 14 (reference to FIG. 10). Next, the heat-resistant high-linear-expansion material 20 is covered with the fiber reinforcing base material 14 from an upper position to be surrounded (reference to FIG. 11).

Step 23:

Referring to FIG. 12, the fiber reinforcing base material 14 and the heat-resistant high-linear-expansion material 20 are covered with auxiliary materials such as sealant 84 and the bag 82, to secure the airtightness between the bag 82 and the jig 80. Note that in the embodiment shown in FIG. 7, the sealant 84 and bag 82 are shown as the auxiliary materials, but other auxiliary materials such as peel ply and breather cloth can be arranged according to need.

Step 24:

A portion which is surrounded by the jig 80 and the bag 82 and in which the fiber reinforcing base material 14 is arranged is evacuated to a vacuum, to apply pushing force to the fiber reinforcing base material 14 by using the atmosphere pressure.

Step 25:

The matrix resin 16 is injected into the portion which has been evacuated to the vacuum, to impregnate the matrix resin 16 into the layers of fiber reinforcing base material 14.

Step 26:

When the matrix resin 16 of the thermosetting type is used, the fiber reinforcing base material 14, the heat-resistant high-linear-expansion material 20 and the matrix resin 16 is heated to the shaping temperature. Then, the matrix resin 16 is cured, taking a predetermined time, to adhere the layers of fiber reinforcing base material 14 to each other. Through this temperature increasing, the heat expands the heat-resistant high-linear-expansion material 20 arranged between the layers of fiber reinforcing base material 14 thermally expand to function as a core so that a predetermined shape is formed on the inside of the interlayer space 23. For example, the curing time in case of thermo shaping is 2-3 hours.

Since the temperature is increased in the condition that the heat-resistant high-linear-expansion material 20 arranged between the layers of fiber reinforcing base material 1 so that the heat-resistant high-linear-expansion material 20 thermally expands, the force which compresses the layers of fiber reinforcing base material 14 from its inside increases. Moreover, by using the heat-resistant high-linear-expansion material 20 having the Shore hardness in the range of A20 to A70, the shapability as the core is maintained and the shape is like to match to the fiber reinforcing base materials 14. Since the force which compresses a fiber reinforcing base material 14 is applied, the porosity (air bubble) which it is easy to generate in case of shaping of the FRP structure 12 having a complicated sectional shape can be decreased to improve the quality of the FRP structure 12.

Step 27:

Referring to FIG. 13, when the predetermined curing time elapses and the matrix resin 16 has been cured, the temperature of the FRP structure 12 is lowered to the room temperature to form the FRP structure 12. After the cooling, a space 22 is formed due to the shrinkage difference between the FRP structure 12 and the heat-resistant high-linear-expansion material (the intermediate structure) 20 at the interlayer space 23 as a result of the difference between the FRP structure 12 and the heat-resistant high-linear-expansion material 20 in the linear expansion coefficient. After that, when the bag 82 is removed and then the heat-resistant high-linear-expansion material 20 is pulled out from the interlayer space 23 of the fiber reinforcing base material 14, the FRP structure 12 shown in FIG. 9 is obtained. Note that s trimming process may be added in which a part of the FRP structure 12 is removed according to need, to take out the heat-resistant high-linear-expansion material 20.

As the material of fiber reinforcing base material 14, carbon fiber, glass fiber, organic fiber such as aramid fiber, polyparaphenylene benzobisoxazole fiber, phenol fiber, polyethylene fiber, and polyvinyl alcohol fiber, metal fiber, and ceramic fiber, or a combination of them. Also, the prepreg material may be used.

Also, a thermoplastic resin or a thermosetting resin can be used as the matrix resin 16. It is desirable to use the thermosetting resin in the current situation from the viewpoint of the shapability and the dynamic characteristic. For example, as the thermosetting resin, epoxy resin, phenol resin, vinyl ester resin, unsaturated polyester resin, cyanate ester resin, bismaleimide resin, benzoxazine resin, other resin may be used. To cure, a curing material, a curing accelerator, a polymerization initiator, a catalyst and so on are added. Moreover, the resin added with an elastomer, rubber and so on can be used. Note that it is desirable that a mold releasing material and resin diffusion media are arranged beforehand on the side of jig 80 and fiber reinforcing base material 14 of the bag. Also, as the thermoplastic resin, for example, PPS (polyphenylene sulfide), PEEK (polyether etherketone), PEKK (polyether ketoneketone), PEK (polyether ketone), PI (polyimide), PEI (polyether imide), PA (nylon polyamide), and so on can be used.

The heat-resistant high-linear-expansion material 20 thermally expands and thermally shrinks according to the curing temperature of the matrix resin 16 in thermo shaping and the room temperature after cooling. The material of the heat-resistant high-linear-expansion material 20 is selected so that the linear expansion coefficient of the heat-resistant high-linear-expansion material 20 is equal to or larger than the linear expansion coefficient of the FRP structure 12. By using the heat-resistant high-linear-expansion material 20 having the large linear expansion coefficient, the heat-resistant high-linear-expansion material 20 can be easily pulled out from the interlayer space 23 of the fiber reinforcing base material 14 without forming a pulling-out taper to the heat-resistant high-linear-expansion material 20. Note that the heat-resistant high-linear-expansion material 20 having pulling-out taper can be used.

To pull out the heat-resistant high-linear-expansion material 20 from the FRP structure 12, it is desirable to select the heat-resistant high-linear-expansion material 20 such that the size of the space formed due to the shrinkage difference between the FRP structure 12 and the heat-resistant high-linear-expansion material 20 after the thermal shrinkage is equal to or larger than the gap of e8 to c9 in the size common difference of clearance fit which is prescribed in JIS B0401.

For example, the case that the length of one side (the basic dimension) of the interlayer space 23 surrounded with the fiber reinforcing base material 14 shown in FIG. 9 is 5 mm is considered. The size common difference of the fit of e8 when the basic dimension is 5 mm is −25 to −47 μm.

For example, it is supposed that the linear expansion coefficient $\Delta 1$ of the FRP structure 12 is $0.2 \times 10^{-6}$ (1/° C.), the linear expansion coefficient $\Delta 2$ of the heat-resistant high-linear-expansion material 20 is $101 \times 10^{-6}$ (1/° C.), the temperature in case of thermo shaping is 180° C., the room temperature after cooling is 15° C., the temperature difference $\Delta T$ is 165° C., and the length (the basic dimension) L of the heat-resistant high-linear-expansion material 20 is 5 mm. In this case, the size of the space 22 formed due to the shrinkage difference is checked.

In this case, the size H of the space formed due to the shrinkage difference is $H = (\Delta 1 - \Delta 2) \times \Delta T \times L \approx -82$ μm. This size H is wider than the size common difference (−25 to −47 μm) of clearance fit of e8 in the reference size. Therefore, the demolding becomes easy in which the heat-resistant high-linear-expansion material 20 is pulled out from the FRP structure 12 after shaping.

The heat-resistant high-linear-expansion material 20 can be used which has the linear expansion coefficient larger than that of the FRP structure by $60 \times 10^{-6}$ (1/° C.) or more. It is desirable to use the heat-resistant high-linear-expansion material 20 having the linear expansion coefficient larger than the linear expansion coefficient of the FRP structure by 100×10$^{-6}$ (1/° C.) or more, more desirably, the linear expansion coefficient larger than the linear expansion coefficient of the FRP structure by 150×10$^{-6}$ (1/° C.) or more, further more desirably, the linear expansion coefficient larger than the linear expansion coefficient of the FRP structure by 200× 10$^{-6}$ (1/° C.) or more. Also, the heat-resistant high-linear-expansion material 20 needs to have the heat resistance to endure the curing temperature (130-500° C. according to the physical property of the resin) of the matrix resin 16 in the thermo shaping shown in FIG. 12.

Also, when the FRP structure 12 is manufactured, the demolding of the heat-resistant high-linear-expansion material 20 in cooling can be promoted by applying the mold releasing material to the surface of the heat-resistant high-linear-expansion material 20 beforehand, in case of arranging the heat-resistant high-linear-expansion material 20 in the fiber reinforcing base material 14.

As shown in FIG. 12, the heat-resistant high-linear-expansion material 20 forms the interlayer space 23 having a predetermined shape between the layers of FRP structure 12 in the thermo shaping. For this purpose, it is desirable that the heat-resistant high-linear-expansion material 20 has hardness to an extent and a high shape precise. Note that when the hardness of the heat-resistant high-linear-expansion material 20 is extremely high, it is expected that the demolding after the shaping becomes difficult. Therefore, it is desirable that the Shore hardness of the heat-resistant high-linear-expansion material 20 is in the range of A20-A70. Note that by using the heat-resistant high-linear-expansion material 20 having a high shape precision, it is possible to form a fine shape on the inner surface of the interlayer space 23 (a bottom of the trapezoidal section and a leg part of the point of an inter section at the embodiments shown in FIG. 11 and FIG. 12) which joins the layers of fiber reinforcing base material 14, as in filets having a predetermined shape.

It is desirable to use silicone rubber and silicone resin which are excellent in demolding, for the the heat-resistant high-linear-expansion material 20. Also, when high heat resistance is necessary, fluororubber can be used. Also, as the material of intermediate heat resistance, natural rubber, butadiene rubber, styrene rubber, butyl rubber, nitrile rubber, ethylene propylene rubber, chrolosulfonated polyethylene rubber and so on can be used. Also, when the heat resistance is unnecessary, a material such as urethane rubber can be used.

It is desirable that the heat-resistant high-linear-expansion material 20 is selected, in consideration of a price, a shaping temperature, chemical resistance to the mold releasing material to be used, a size of the space 22 formed based on the shrinkage difference (a difference from the linear expansion coefficient of FRP structure 12) and so on.

The compounds of fluorine system and silicon system can be used for the mold releasing material.

In the above-mentioned embodiment, the embodiment in which the resin of a thermosetting type is used as the matrix resin 16 has been described. The present invention can be applied to the FRP structure 12 using the resin of a thermoplastic type.

By using the heat-resistant high-linear-expansion material 20 as the core which shapes the interlayer space 23 of the FRP structure 12, the interlayer space 23 having a small cross section and the interlayer space 23 having a complicated sectional shape can be formed at low cost.

Fourth Embodiment

In the above-mentioned third embodiment, the FRP structure 12 using the fiber reinforcing base material 14 has been described. On the other hand, in a fourth embodiment, the FRP structure 12P using prepreg material 14P will be described.

Figure 14:
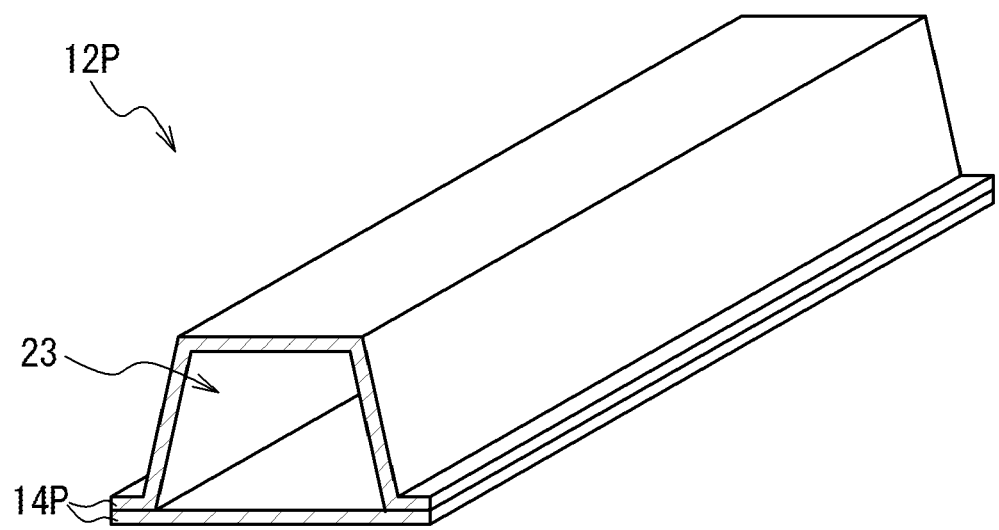
FIG. 14 is a perspective view of an outward appearance of the FRP structure which has an interlayer space surrounded with two layers of prepreg materials, after completion.

FIG. 14 is a perspective view showing an outward appearance of the FRP structure having the interlayer space 23 surrounded by two layers of prepreg material 14P.

Referring to FIG. 14, the FRP structure 12P has a plurality of layers of prepreg material 14P and the heat-resistant high-linear-expansion material 20 and the interlayer space 23 surrounded by the prepreg material 14P.

The FRP structure is a structure member such as a stringer and a mold, in which the plurality of layers of prepreg material 14P are stacked and cured.

Figure 15:
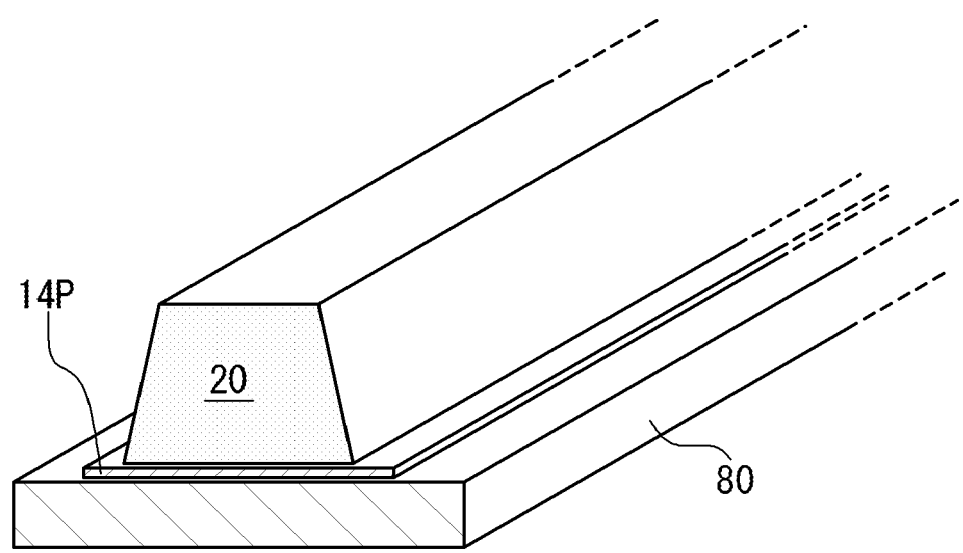
FIG. 15 is a diagram showing the condition that the prepreg material and the heat-resistant high-linear-expansion material are arranged on the jig for shaping.
Figure 16:
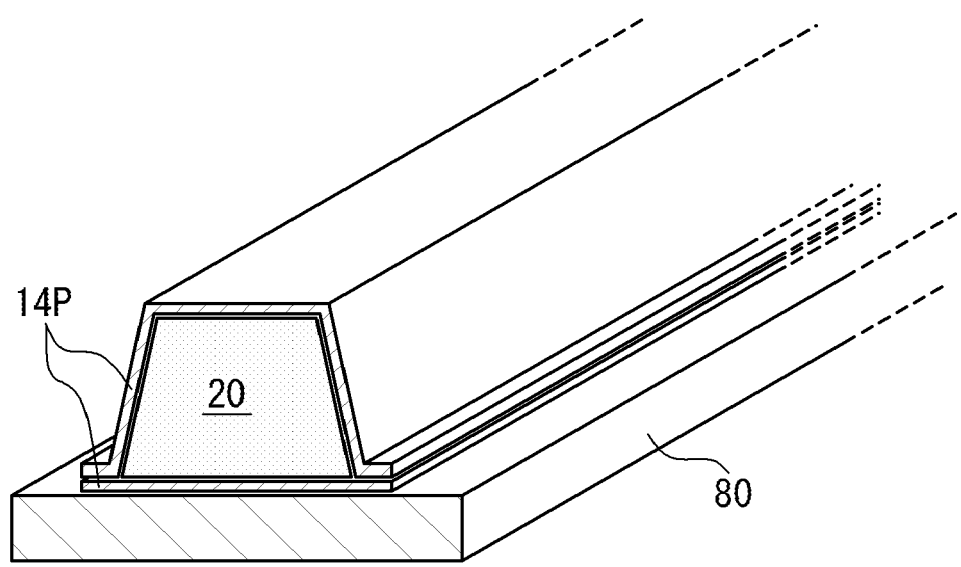
FIG. 16 is a diagram showing the condition that the prepreg material is arranged on the heat-resistant high-linear-expansion material to surround the heat-resistant high-linear-expansion material.
Figure 17:
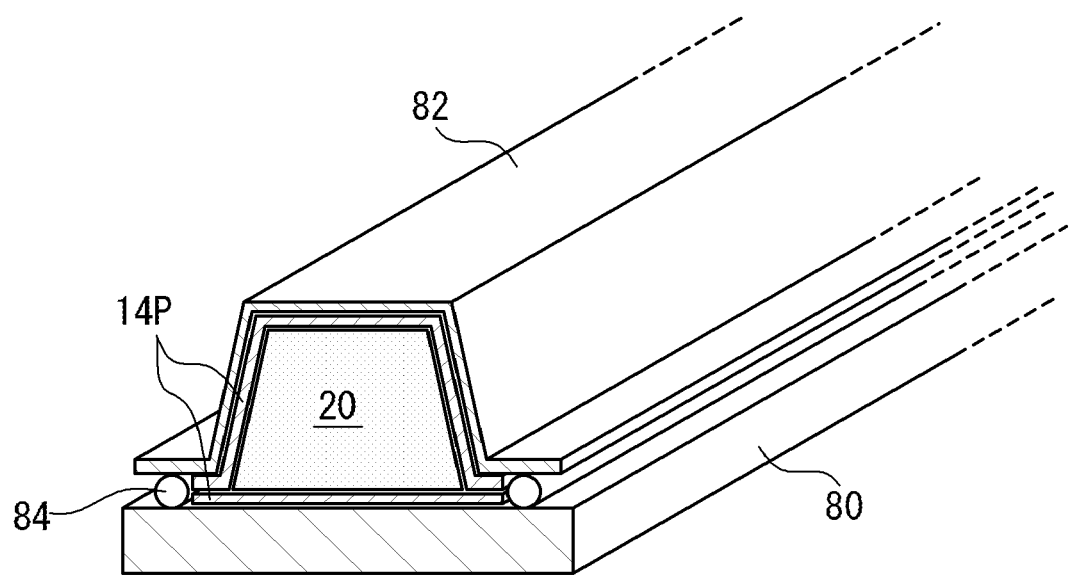
FIG. 17 is a diagram showing the thermo shaping in which a plurality of prepreg materials and the heat-resistant high-linear-expansion material are covered with the bag to secure airtightness between the bag and the jig.
Figure 18:
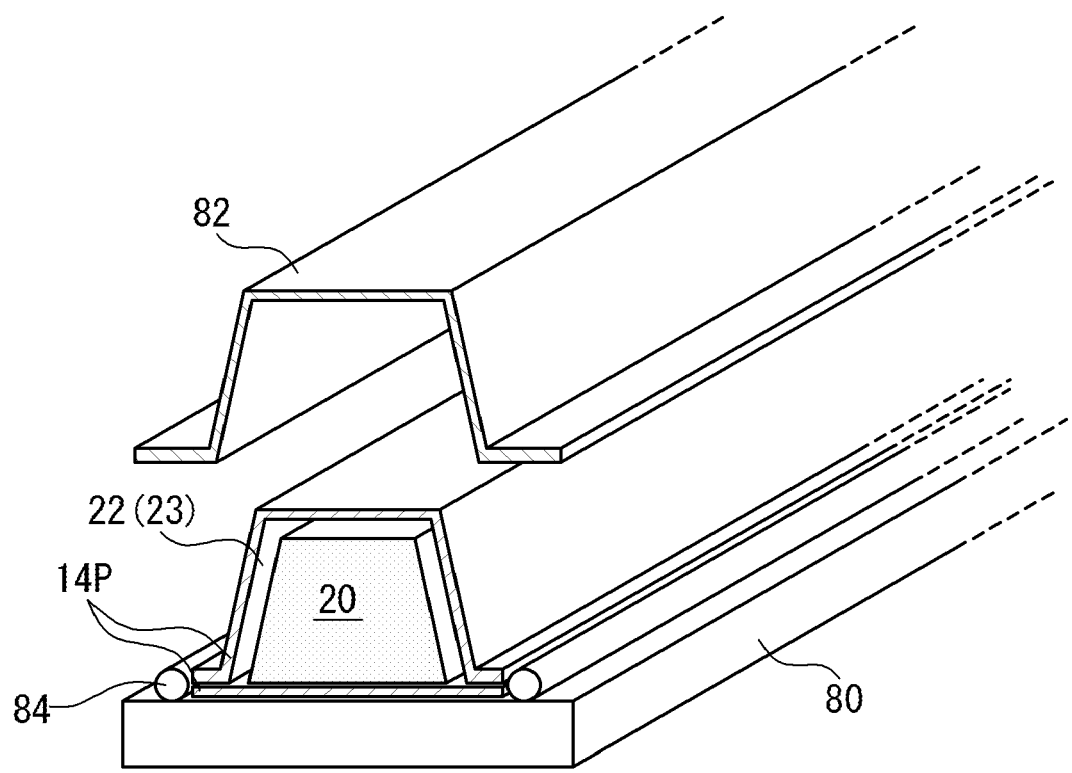
FIG. 18 is a diagram showing the condition that the bag is removed in the room temperature after shaping the FRP structure.

Next, a method of manufacturing the FRP structure 12P shown in FIG. 14 will be described with reference to FIG. 15 to FIG. 18. FIG. 15 is a diagram showing a state that the layers of prepreg material 14P and the heat-resistant high-linear-expansion material 20 are arranged on the jig 80 for the shaping. FIG. 16 is a diagram showing a state that the layers of prepreg material 14P are arranged on the heat-resistant high-linear-expansion material 20 to be surrounded. FIG. 17 is a diagram showing a state of the thermo shaping when the plurality of layers of prepreg material 14P and the heat-resistant high-linear-expansion material 20 are covered with the bag 82 to secure the airtightness between the bag 82 and the jig 80. FIG. 18 is a diagram showing a state that the bag 82 is removed in the room temperature after shaping of the FRP structure 12P.

The method of manufacturing the FRP structure 12P shown in FIG. 14 includes:

Step 31: arranging the plurality of layers of prepreg material 14P;

Step 32: arranging the heat-resistant high-linear-expansion material 20 between the layers of prepreg material 14P;

Step 33: covering the plurality of layers of prepreg material with the bag 82;

Step 34: evacuating the inside of the bag 82, in which the prepreg material 14P is arranged, to a vacuum;

Step 35: heating the prepreg material 14P and the heat-resistant high-linear-expansion material 20 to the shaping temperature which is higher than the room temperature to shape the FRP structure; and Step 36: lowering to the room temperature after shaping of the FRP structure.

Step 31:

Referring to FIG. 15, when the FRP structure 12P should be shaped, the layers of prepreg material 14P are stacked and arranged on the jig 80 having a predetermined shape.

Step 32:

The mold releasing material is applied to the surface of the heat-resistant high-linear-expansion material 20 according to need. Then, the heat-resistant high-linear-expansion material 20 with a predetermined size is arranged in a predetermined position between the layers of prepreg material 14P (reference to FIG. 15). Next, the layers of prepreg material 14P are arranged on the heat-resistant high-linear-expansion material 20 to surround it (reference to FIG. 16).

Step 33:

Referring to FIG. 17, the plurality of layers of prepreg material 14P and the heat-resistant high-linear-expansion material 20 are covered with the auxiliary materials such as sealant 84 and bag 82 so as to secure the airtightness between the bag 82 and the jig 80. In the embodiment shown in FIG. 7, the sealant 84 and the bag 82 are shown as the auxiliary materials, but a peel ply, breather cloth, and the other auxiliary materials can be arranged according to need.

Step 34:

A portion which is surrounded with the jig 80 and the bag 82 and in which the prepreg material 14P is arranged is evacuated to the vacuum so as to apply a pushing force to the prepreg material 14P by using the atmosphere pressure.

Step 35:

The temperatures of the plurality of layers of prepreg material 14P and the heat-resistant high-linear-expansion material 20 are increased to the shaping temperature, and the matrix resin is cured by taking a predetermined time. This temperature increasing expands the heat-resistant high-linear-expansion material 20 arranged between the layers of prepreg material 14P to make it function as the core, so that the inner surface of the interlayer space 23 is shaped to have a predetermined shape.

When the temperature is increased in the condition that the heat-resistant high-linear-expansion material 20 is arranged between the layers of prepreg material 14P, the heat-resistant high-linear-expansion material 20 expands so that the force of compressing the layers of prepreg material 14P increases.

Step 36:

Referring to FIG. 18, the temperature of the FRP structure 12P is lowered to the room temperature, after the predetermined curing time elapses to cure the matrix resin. After cooling, the space has been formed between the FRP structure 12P the heat-resistant high-linear-expansion material 20 in the interlayer space 23 due to the shrinkage difference as a result of the difference between the linear expansion coefficient of the FRP structure 12P and the linear expansion coefficient of the heat-resistant high-linear-expansion material 20. After that, the bag 82 is removed and the heat-resistant high-linear-expansion material 20 is pulled out from the interlayer space 23 of the prepreg material 14P, resulting in that the FRP structure 12P shown in FIG. 14 is obtained.

The same material used in the above third embodiment can be used as the heat-resistant high-linear-expansion material 20, the mold releasing material, the heat-resistant high-linear-expansion material 20, the jig 80, the bag 82, and so on.

Fifth Embodiment

In the above-mentioned third embodiment, the FRP structure 12 in which the interlayer space 23 in one location is formed has been described. On the other hand, in the fifth embodiment, an example that a plurality of interlayer spaces 23 are shaped in the FRP structure 13.

Figure 19:
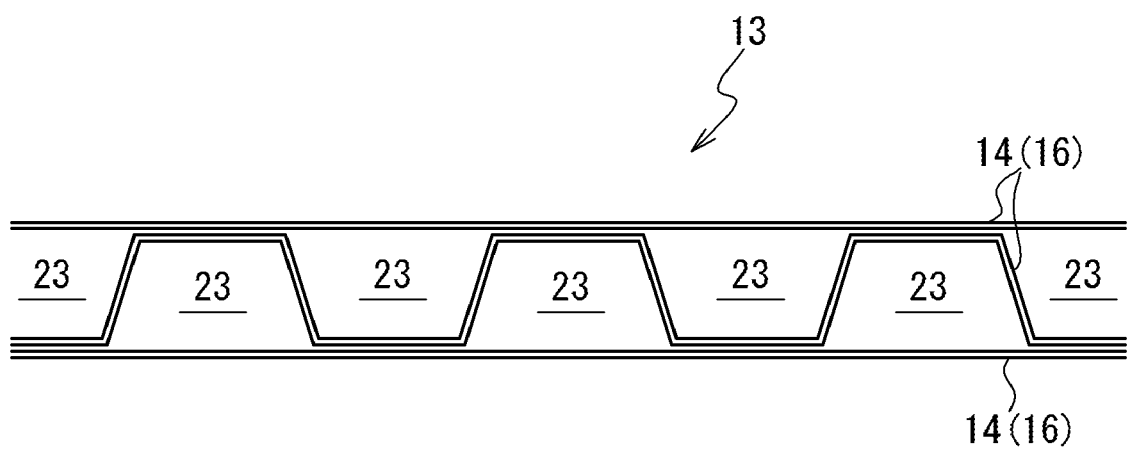
FIG. 19 is a side view showing the FRP structure in which a plurality of interlayer spaces are formed in the interlayer surrounded by the fiber reinforcing base material, after completion.

FIG. 19 is a side view of the FRP structure 13 which a plurality of interlayer spaces 23 have been formed to be surrounded with the fiber reinforcing base material 14. Conventionally, many processes are needed to shape the structure material of a corrugate sandwich structure as shown in FIG. 19 and expensive tools such as a divisional type of mold must be used.

A method of manufacturing the FRP structure 13 shown in FIG. 19 will be described below with reference to FIG. 20 and FIG. 21.

Figure 20:
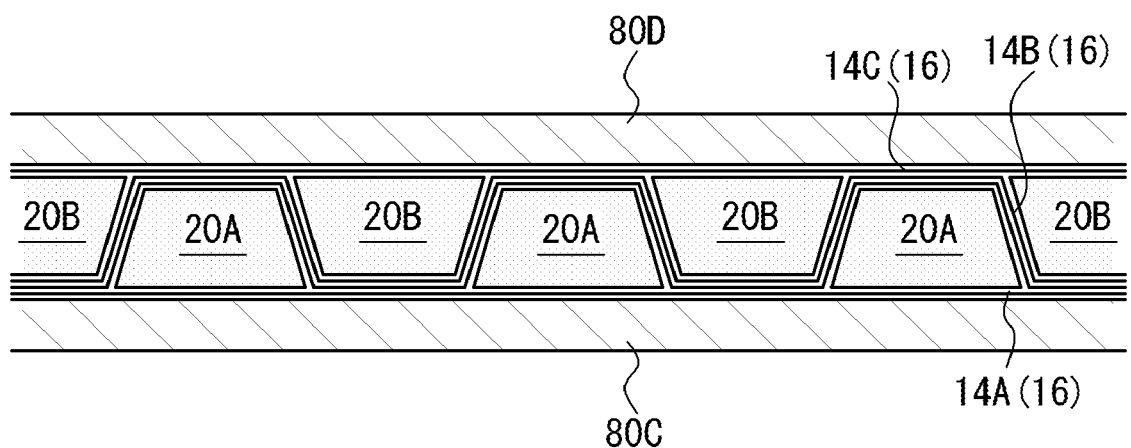
FIG. 20 is a diagram showing the thermo shaping in which the fiber reinforcing base material and the heat-resistant high-linear-expansion material are arranged between a lower-side jig and an upper-side jig.

FIG. 20 is a diagram showing the thermo shaping when the fiber reinforcing base materials 14, 14A, 14B, and 14C, and the heat-resistant high-linear-expansion material 20A and 20B are arranged between the lower-side jig 80C and the upper-side jig 80D. FIG. 21 is a diagram showing the FRP structure 13 cooled to the room temperature after shaping and removed with the lower-side jig 80C, the upper-side jig 80D and the bag.

A method of manufacturing the FRP structure 13 shown in FIG. 19 includes:

Step 41: arranging the fiber reinforcing base materials 14A, 14B, and 14C;

Step 42: covering them and evacuating the inside of the bag to a vacuum;

Step 43: impregnating the matrix resin 16 and shaping the FRP structure 13 in the shaping temperature; and Step 44: a demolding step of lowering to the room temperature after shaping of the FRP structure 13.

Step 41:

When the FRP structure 13 having a plurality of interlayer spaces 23 should be shaped, the fiber reinforcing base material 14A is arranged and stacked on the jig 80C having a predetermined shape as shown in FIG. 20. Then, a plurality of heat-resistant high-linear-expansion materials 20A are arranged the fiber reinforcing base material 14A at predetermined intervals. Next, the fiber reinforcing base material 14B is arranged to cover the heat-resistant high-linear-expansion materials 20A to form a corrugation structure. Next, the heat-resistant high-linear-expansion materials 20B are arranged in valley sections of the fiber reinforcing base material 14B arranged to have the corrugation structure. Next, the fiber reinforcing base material 14C is arranged on the heat-resistant high-linear-expansion materials 20B and the fiber reinforcing base material 14B. Then, the jig 80D is arranged on the fiber reinforcing base material 14C. The mold releasing material is applied to the surface of the heat-resistant high-linear-expansion materials 20A and 20B beforehand, according to need.

Step 42:

Next, the fiber reinforcing base materials 14A, 14B, and 14C, the heat-resistant high-linear-expansion material (the intermediate structure) 20A and 20B, and the jigs, 80C and 80D are covered with the bag (not shown) so as to secure the airtightness. Then, the inside of the bag is evacuated to the vacuum and the pushing force is applied to the fiber reinforcing base material 14 by using the atmosphere pressure.

Step 43:

Next, the matrix resin 16 is injected into the portion that has been evacuated to the vacuum, to impregnate the matrix resin 16 to the fiber reinforcing base materials 14A, 14B, and 14C. When the matrix resin 16 of the thermosetting type is used, the fiber reinforcing base materials 14A, 14B, and 14C, the heat-resistant high-linear-expansion materials 20A and 20B and the matrix resin 16 are heated to the shaping temperature, and the matrix resin 16 is cured while the predetermined time elapses to unify the fiber reinforcing base materials 14A, 14B, and 14C. The heat-resistant high-linear-expansion materials 20A and 20B arranged between corresponding two of the fiber reinforcing base materials 14A, 14B, and 14C thermally expand through this temperature increasing to function as the cores, and to form the shapes of the insides of the interlayer spaces 23 (reference to FIGS. 19 and 12).

Figure 21:
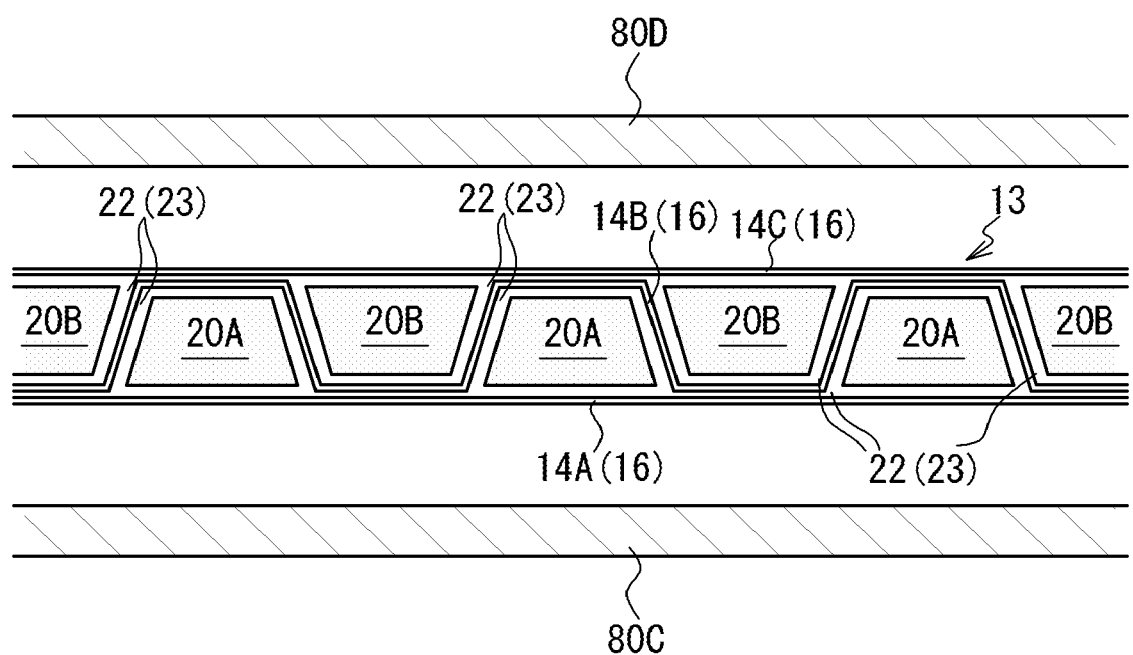
FIG. 21 is a diagram showing the condition that the upper-side jig, the lower-side jig and the bag are removed in the room temperature after shaping the FRP structure.

Step 44:

Referring to FIG. 21, after the predetermined curing time has elapsed and the matrix resin 16 has cured, the temperature of FRP structure 13 is lowered to the room temperature. At this time, the spaces 20 are formed at the interlayer spaces 23 due to the shrinkage difference between the FRP structure 13 and the heat-resistant high-linear-expansion materials 20A and 20B as the result of the difference between the linear expansion coefficient of the FRP structure 13, and the linear expansion coefficients of the heat-resistant high-linear-expansion materials 20A and 20B. After that, the bag and the jigs 80C and 80D are removed, and the heat-resistant high-linear-expansion materials 20A and 20B are pulled out from the interlayer spaces 23 of the fiber reinforcing base materials 14A, 14B, and 14C. As a result, the FRP structure 13 shown in FIG. 19 is obtained.

As show in FIG. 20, since the heat-resistant high-linear-expansion materials 20A and 20B thermally expands in the thermo shaping to increase the volume, the heat-resistant high-linear-expansion materials 20A and 20B function as the cores to form the interlayer spaces 23 with predetermined shapes at the interlayers of the FRP structure 13.

After cooling, as shown in FIG. 21, the heat-resistant high-linear-expansion materials 20A and 20B thermally shrinks to decrease the volume (note that in FIG. 21, the thermal shrinkage of the heat-resistant high-linear-expansion materials 20A and 20B are shown exaggeratingly). At this time, the predetermined shapes are formed at the interlayers of the FRP structure 13, and the spaces 22 are formed due to the shrinkage difference between the FRP structure 13 and each of the heat-resistant high-linear-expansion materials 20A and 20B. By forming the spaces due to the shrinkage difference, the heat-resistant high-linear-expansion materials 20A and 20B functioning as the cores can be easily pulled out from the interlayer spaces 23 of the FRP structure 13.

The heat-resistant high-linear-expansion materials (the intermediate structure) 20A and 20B having the linear expansion coefficient larger than that of the FRP structure 13 by $60 \times 10^{-6}$ (1/° C.) can be used, desirably, by $100 \times 10^{-6}$ (1/° C.), more desirably, by $150 \times 10^{-6}$ (1/° C.), and further more desirably, by $200 \times 10^{-6}$ (1/° C.)

The physical property required for the heat-resistant high-linear-expansion materials 20A and 20B is the same as that of the heat-resistant high-linear-expansion material 20 described in the third embodiment. Also, the physical property required for the mold releasing material to be applied to the surfaces of the heat-resistant high-linear-expansion materials 20A and 20B is the same as that of the mold releasing material described in the third embodiment.

By using the heat-resistant high-linear-expansion materials 20A and 20B as the cores to shape the interlayer spaces 23 of the FRP structure 13, the FRP structure 13 with the many interlayer spaces 23 having a small section area and with the many interface spaces 23 having complicated sectional shapes can be shaped in a low cost.

Sixth Embodiment

In the above-mentioned fifth embodiment, the FRP structure 13 using the fiber reinforcing base material 14 has been described. On the other hand, in a sixth embodiment, the FRP structure using the prepreg material 14P will be described.

Figure 22:
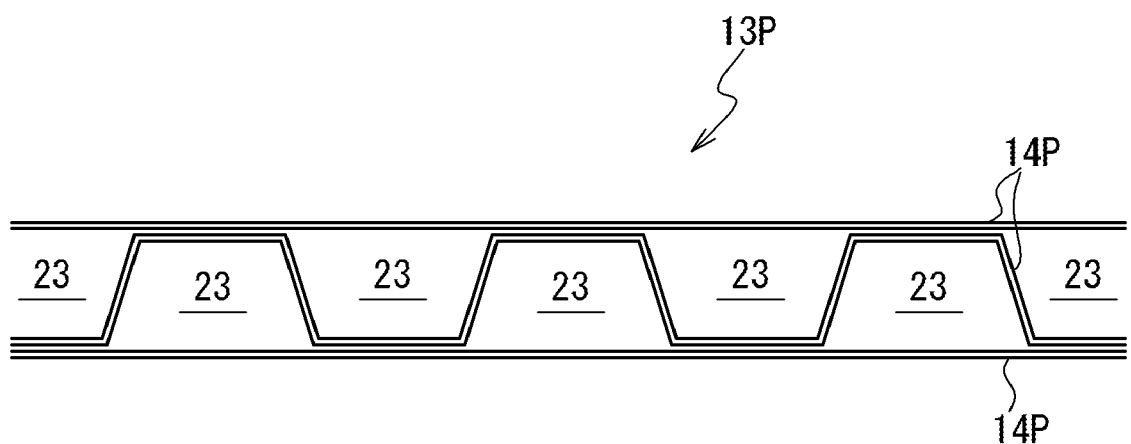
FIG. 22 is a side view showing the FRP structure which a plurality of interlayer spaces are formed in the interlayer surrounded with the layers of prepreg material, after completion.

FIG. 22 is a side view showing the FRP structure 13P in which the plurality of interlayer spaces 23 are formed at the layers surrounded by the prepreg material 14P (prepreg material 14Q, 14R, and 14S).

A method of manufacturing the FRP structure 13P shown in FIG. 22 will be described below with reference to FIG. 23 and FIG. 24.

Figure 23:
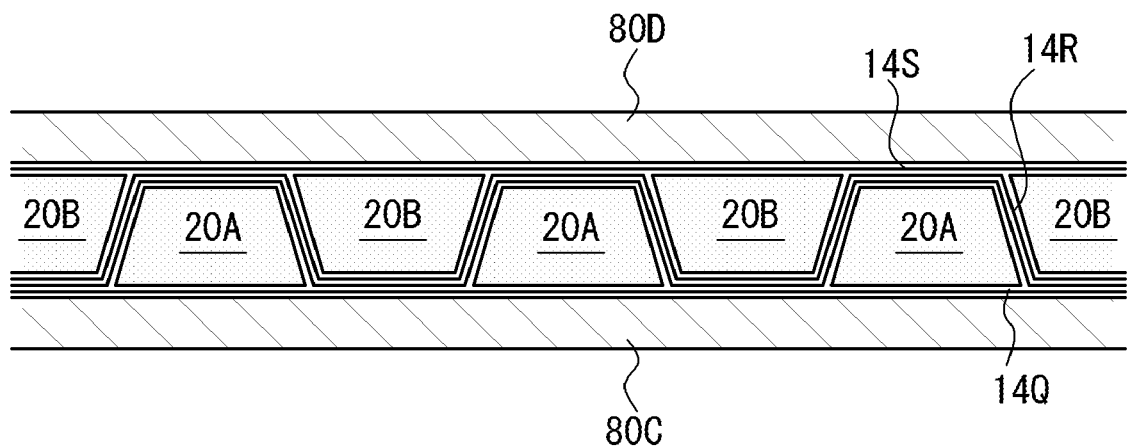
FIG. 23 is a diagram showing the condition of thermo shaping that the prepreg material and the heat-resistant high-linear-expansion material between the lower-side jig and the upper-side jig.

FIG. 23 is a diagram showing the state of thermo shaping in which the prepreg materials 14Q, 14R, and 14S and the heat-resistant high-linear-expansion material 20 are arranged between the lower-side jig 80C and the upper-side jig 80D. FIG. 24 is a diagram showing the state when the lower-side jig 80C, the upper-side jig 80D and the bag are removed in the room temperature after shaping the FRP structure 13P.

A method of manufacturing the FRP structure 13P shown in FIG. 22 includes:
Step 51: arranging the prepreg materials 14P, 14Q, 14R, and 14S;
Step 52: shaping the FRP structure 13P the shaping temperature; and
Step 53: lowering to the room temperature after shaping of the FRP structure 13P.

Step 51:

When the FRP structure 13P having the plurality of interlayer spaces 23 should be shaped, the prepreg material 14Q is stacked and arranged on the jig 80C having a predetermined shape as shown in FIG. 23. Then, the plurality of heat-resistant high-linear-expansion materials 20A are arranged at predetermined intervals on the prepreg material 14Q. Next, the prepreg material 14R is arranged on the heat-resistant high-linear-expansion material (the intermediate structure) 20A to cover it so as to have the corrugation structure. Next, the heat-resistant high-linear-expansion materials 20B are arranged in the valley sections of the prepreg material 14R arranged to have the corrugation structure. Next, the prepreg material 14S is arranged on the heat-resistant high-linear-expansion material (the intermediate structure) 20B and the prepreg material 14R. Then, the jig 80D is arranged on the prepreg material 14S. The mold releasing material is applied to the surfaces of the heat-resistant high-linear-expansion materials 20A and 20B beforehand according to need. Also, the adhesive material may be arranged beforehand on bonding surfaces between the prepreg materials 14Q, 14R, 14S, according to need.

Next, the prepreg materials 14Q, 14R, and 14S, the heat-resistant high-linear-expansion materials 20A and 20B, and the jigs 80C and 80D are covered with the bag (not shown) to secure airtightness. Then, the inside of the bag is evacuated to a vacuum to apply pushing force to the prepreg materials 14Q, 14R, and 14S by using the atmosphere pressure.

Step 52:

Next, the prepreg materials 14Q, 14R, and 14S, and the heat-resistant high-linear-expansion materials 20A and 20B are heated to the shaping temperature and cured in the predetermined time, to unify the prepreg materials 14Q, 14R, and 14S. Through the temperature increasing, the heat-resistant high-linear-expansion materials 20A and 20B arranged between the layers of prepreg materials 14Q, 14R, and 14S thermally expands to function as the core and to shape the inside of the interlayer space 23 (reference to FIGS. 22 and 23).

Figure 24:
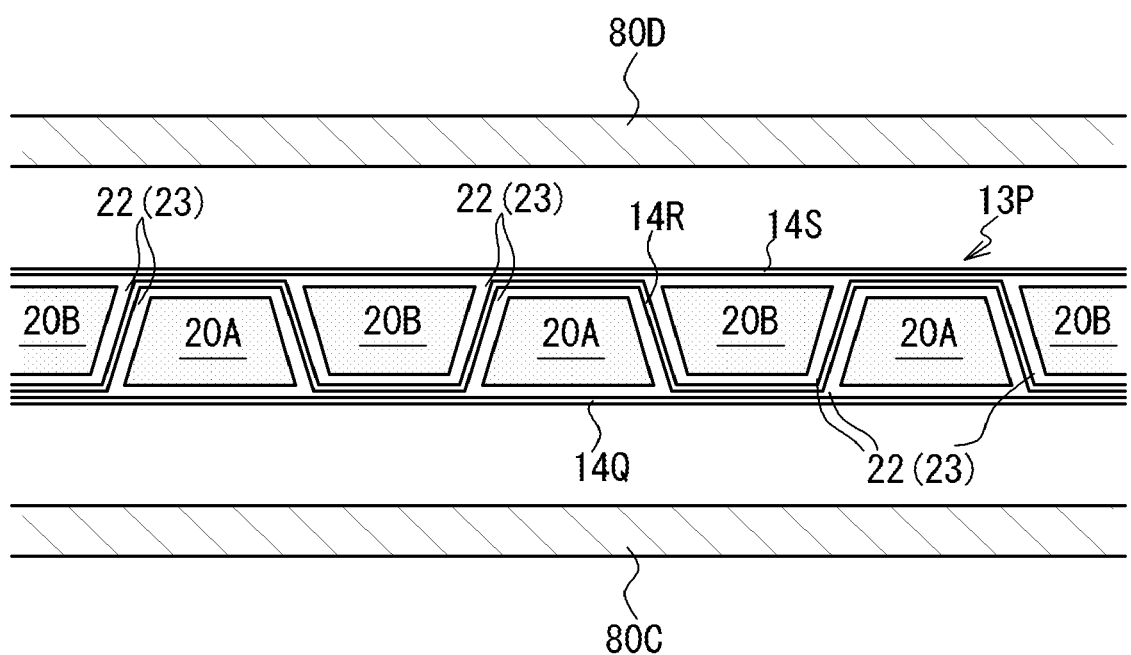
FIG. 24 is a diagram showing the FRP structure when the lower-side jig, the upper-side jig, and the bag are removed in the room temperature after shaping.

Step 53:

Referring to FIG. 24, the temperature of the FRP structure 13P is lowered to the room temperature when the predetermined curing time elapses so as to cure the prepreg materials 14Q, 14R, and 14S. At that time, the spaces are formed due to the shrinkage difference between the FRP structure 13P and the heat-resistant high-linear-expansion materials 20A and 20B in the interlayer spaces 23 as a result of the difference between the FRP structure 13P and the heat-resistant high-linear-expansion materials 20A and 20B in the linear expansion coefficient. After that, the bags and the jigs 80C and 80D are removed. When the heat-resistant high-linear-expansion materials 20A and 20B are pulled out from the interlayer spaces 23 of the prepreg materials 14Q, 14R, and 14S, the FRP structure 13P shown in FIG. 22 is obtained.

Show in FIG. 23, since of the heat-resistant high-linear-expansion materials 20A and 20B thermally expand in the thermo shaping to increase the volume, the heat-resistant high-linear-expansion materials 20A and 20B function as the cores to form the interlayer spaces 23 with predetermined shapes in the interlayers of the FRP structure 13P.

After cooling, as show in FIG. 24, the heat-resistant high-linear-expansion materials 20A and 20B thermally shrink to decrease the volumes (note that in FIG. 24, the thermal shrinkage of the heat-resistant high-linear-expansion materials 20A and 20B are exaggerated for the convenience of explanation). At this time, the spaces are formed due to the shrinkage difference between the predetermined shape of the interlayers of the FRP structure 13P and the heat-resistant high-linear-expansion materials 20A and 20B. Thus, the heat-resistant high-linear-expansion materials 20A and 20B functioning as the cores can be easily pulled out from the interlayer spaces 23 of the FRP structure 13P.

The heat-resistant high-linear-expansion material 20, the mold releasing material, the prepreg materials 14, the jigs 80, the bag 82, and so on which are identical in the above fifth embodiment can be used.

(Conventional Method of Manufacturing FRP Structure)

Figure 25:
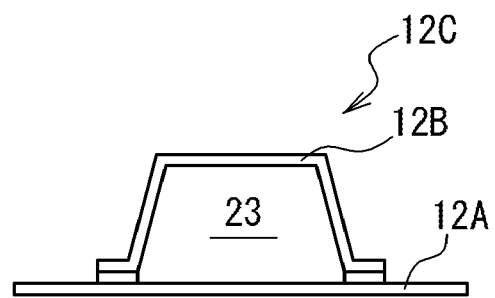
FIG. 25 is a side view showing a conventional FRP structure that plural kinds of FRP intermediate structures are combined.
Figure 26A:
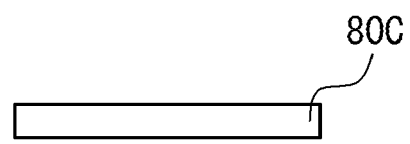
FIG. 26A is a side view showing a preparation process of the lower-side jig used when the conventional FRP intermediate structure is shaped.
Figure 26B:
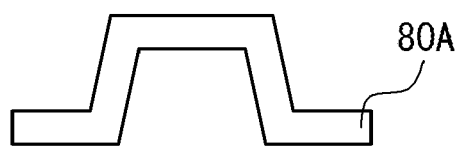
FIG. 26B is a side view showing a preparation process of the lower-side jig used when the conventional FRP intermediate structure is shaped.
Figure 27A:
FIG. 27A is a side view showing a conventional layer stacking process of arranging the layers of prepreg material on the lower-side jig.
Figure 27B:
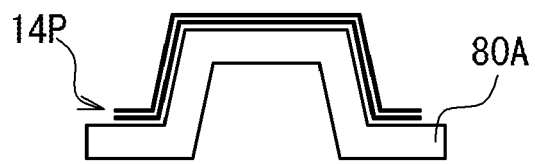
FIG. 27B is a side view showing a conventional layer stacking process of arranging the layers of prepreg material on the lower-side jig.

Here, a conventional method of manufacturing an FRP structure 12C will be described with reference to FIG. 25 to FIG. 31. FIG. 25 is a side view showing a conventional FRP structure 12C by combining FRP intermediate structures 12A and 12B. FIG. 26A and FIG. 26B are side views showing preparing processes of the lower-side jigs 80A and 80A used to shape the conventional FRP intermediate structures 12A and 12B. FIG. 27A and FIG. 27B are side views showing conventional stacking processes of arranging and stacking the prepreg material 14P on the lower-side jigs 80C and 80A.

Figure 28A:
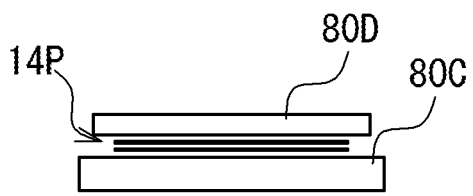
FIG. 28A is a side view showing a conventional jig setting process of setting the upper-side jig on the stacked prepreg material.
Figure 28B:
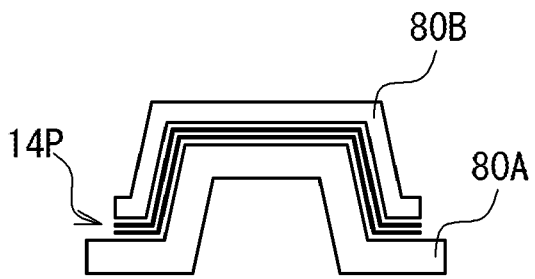
FIG. 28B is a side view showing a conventional jig setting process of setting the upper-side jig on the stacked prepreg material.
Figure 29A:
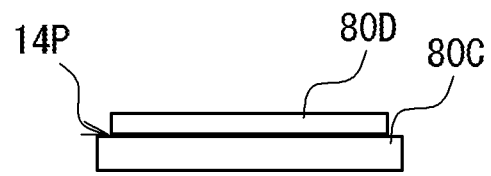
FIG. 29A is a side view showing a conventional curing process of thermally curing the matrix resin.
Figure 29B:
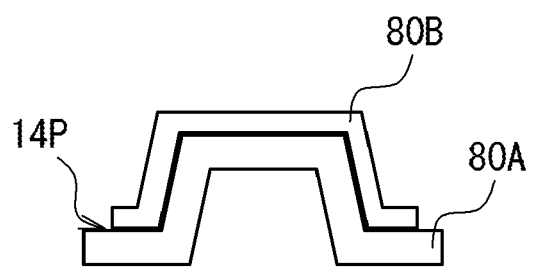
FIG. 29B is a side view showing a conventional curing process of thermally curing the matrix resin.
Figure 30A:
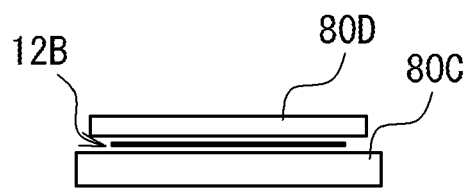
FIG. 30A is a side view showing a conventional demolding process.
Figure 30B:
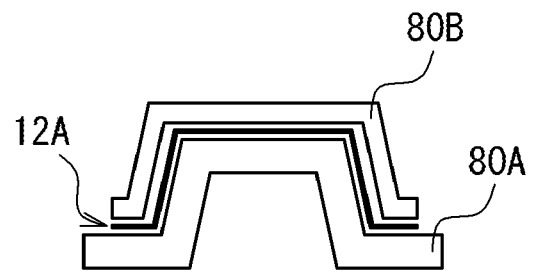
FIG. 30B is a side view showing a conventional demolding process.
Figure 31:
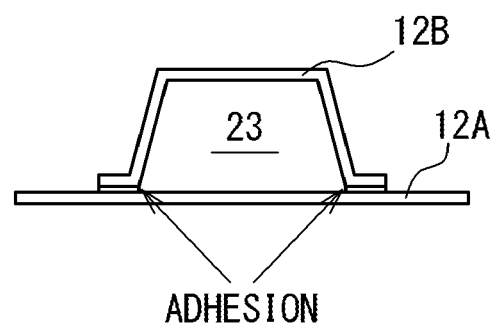
FIG. 31 is a diagram showing a conventional adhering process of bonding the FRP intermediate structures with an adhesive material.

FIG. 28A and FIG. 28B are side views showing conventional jig setting processes of installing the jig 80D, 80B on the prepreg material 14P. FIG. 29A and FIG. 29B are side views showing conventional curing processes of thermally curing the prepreg material 14P in a furnace. FIG. 30A is a side view showing a conventional demolding process of removing the jigs 80C and 80D from the FRP intermediate structure 12B. FIG. 30B is a side view showing a conventional demolding process of removing the jig 80A and 80B from the FRP intermediate structure 12A. FIG. 31 is a diagram showing an adhering process of the conventional FRP intermediate structures 12A and 12B with an adhesive material.

Referring to the conventional jig preparing process shown in FIG. 26A and FIG. 26B, the lower-side jigs 80C, 80A (a mold, an FRP structure jig and so on) are respectively prepared for the FRP intermediate structures 12B and 12A.

Next, referring to the conventional layer stacking process shown in FIG. 27A and FIG. 27B, the prepreg material 14P are respectively arranged on the lower-side jigs 80C and 80A.

Next, referring to the conventional jig setting process shown in FIG. 28A and FIG. 28B, the jigs 80D and 80B (the mold, the FRP structure jig and so on) are set on the prepreg material 14P. Then, the jig 80A to the jig 80D and the prepreg material 14P are covered with the bag (not shown).

Next, referring to the conventional curing process shown in FIG. 29A and FIG. 29B, the curing (the autoclave shaping) process is carried out of curing the prepreg material 14P by heating the prepreg material 14P to the shaping temperature higher than the room temperature in the furnace.

If the prepreg material 14P has cured, the temperature of the FRP intermediate structures 12A and 12B are lowered to the room temperature and the bag is removed. Next, as in the conventional demolding process shown in FIG. 30A and FIG. 30B, the FRP intermediate structures 12A and 12B are obtained by removing the jigs 80A and the jig 80D and carrying out the demolding.

Next, referring to FIG. 31, the FRP intermediate structures 12A and 12B are combined and adhered. When the adhesive material has cured, the FRP structure 12C shown in FIG. 25 is completed.

As mentioned above, when the FRP structure 12C is manufactured to have the interlayer spaces 23, it conventionally needed to form the FRP intermediate structures 12A and 12B. Also, although it is possible to shape the FRP structure at once by using a divisional type core without shaping the FRP intermediate structures 12A and 12B, the structure of a divisional type of core is complicated and it takes many man-days for the maintenance. Therefore, a high cost was necessary to manufacture the FRP structure 12C having the interlayer spaces 23.

As shown in the third embodiment to the sixth embodiment, by using the heat-resistant high-linear-expansion material 20 as the core for shaping the interlayer spaces 23 of the FRP structures 12 and 13, the interlayer spaces 23 with a small sectional area and the interlayer space 23 with a complicated sectional shape can be shaped at a low cost.

As such, the artificial defect material and the manufacturing method of the FRP structure according to the present invention have been described with reference to the embodiments. The artificial defect material and the manufacturing method of the FRP structure according to the present invention are not limited to the above embodiments. Various changes can be carried out to the above embodiments. The technical matters described in one of the embodiments and the technical matter described in the other of the embodiments may be combined.

Also, the FRP structure which is shaped by using the manufacturing method of the FRP structure according to the present invention is used for various fields such as vehicles, ships, and aircrafts and architecture members. The artificial defect material and the manufacturing method of the FRP structure according to the present invention are suitable when two or more fiber reinforcing base materials are combined to shape the complicated final shape having a closed space. Also, the artificial defect material and the manufacturing method of the FRP structure according to the present invention can be used for shaping the FRP structure by the RFI (resin film infusion shaping method) method, the RTM (resin transfer shaping method) method, the VaRTM (vacuum impregnation method) method, the autoclave method, and so on.

The invention claimed is:

1. A method of manufacturing an FRP structure comprising:
arranging a structure having a plurality of structure layers to include a first intermediate structure between a first structure layer and a second structure layer, which are always adjacent, of the plurality of structure layers, each of which comprises a fiber reinforcing base material;
heating the structure to a thermally curing temperature of thermosetting resin contained in the plurality of structure layers such that the structure is shaped based on a shape of the first intermediate structure in case of thermally expanding; and
cooling the structure to a room temperature,
wherein the first intermediate structure maintains the shape while expanding in case of heating to the thermally curing temperature, and returns to an original shape in case of cooling to the room temperature, and has a linear expansion coefficient larger than that of the thermosetting resin by a predetermined value or more.

2. The method of manufacturing an FRP structure according to claim 1, wherein Shore hardness of the first intermediate structure is in a range of A20 to A70.

3. The method of manufacturing an FRP structure according to claim 1, wherein the first intermediate structure is formed of a material selected from a group consisting of silicone rubber, silicone resin, fluororubber, natural rubber, butadiene rubber, styrene rubber, butyl rubber, nitrile rubber, ethylene propylene rubber, chlorosulfonated polyethylene rubber, and urethane rubber.

4. The method of manufacturing an FRP structure according to claim 1, wherein each of the plurality of structure layers is a prepreg material layer containing a thermosetting resin.

5. The method of manufacturing an FRP structure according to claim 1, wherein the arranging comprises:
injecting matrix resin as the thermosetting resin into the structure so as to impregnate a fiber reinforcing base material each of the plurality of structure layers and to cover the first intermediate structure.

6. The method of manufacturing an FRP structure according to claim 1, wherein the plurality of structure layers has a third structure layer neighboring the second structure layer,
wherein the first structure layer, the second structure layer, and the third structure layer are stacked,
wherein the arranging a structure comprises:
arranging the first intermediate structure between the first structure layer and the second structure layer; and
arranging the second intermediate structure between the second structure layer and the third structure layer,
wherein the second intermediate structure maintains its shape while expanding, in case of heating to the heat curing temperature, returns to the original shape in case of cooling to the room temperature, and has the linear expansion coefficient larger than that of the thermosetting resin by the predetermined value or more.

7. The method of manufacturing an FRP structure according to claim 6, wherein the second structure layer is a corrugated type structure layer, and the first structure layer and the third structure layer are flat structure layers, and
wherein the first intermediate structure and the second intermediate structure are alternately and repeatedly arranged.

8. The method of manufacturing an FRP structure according to claim 6, further comprising:
pulling out the first intermediate structure and the second intermediate structure after the cooling.

9. The method of manufacturing an FRP structure according to claim 8, further comprising:
applying a mold releasing material of a silicon system or a fluorine system to a surface of the first intermediate structure and a surface of the second intermediate structure, before the arranging.

10. The method of manufacturing an FRP structure according to claim 6, wherein Shore hardnesses of the first intermediate structure and the second intermediate structure are in a range of A20 to A70.

11. The method of manufacturing an FRP structure according to claim 6, wherein each of the first intermediate structure and the second intermediate is formed of a material selected from the group consisting of silicone rubber, silicone resin, fluororubber, natural rubber, butadiene rubber, styrene rubber, butyl rubber, nitrile rubber, ethylene propylene rubber, chlorosulfonated polyethylene rubber and urethane rubber.

12. The method of manufacturing an FRP structure according to claim 1, the predetermined value is $100 \times 10^{-6}$ (1/° C.).

13. The method of manufacturing an FRP structure according to claim 12, wherein the predetermined value is $150 \times 10^{-6}$ (1/° C.).

14. An artificial defect material comprising:
a plurality of layers of prepreg material; and
an intermediate structure,
wherein the intermediate structure is arranged between at least one pair of always adjacent layers of the prepreg material,
wherein the intermediate structure has heat resistance at a shaping temperature higher than the room temperature and a property of keeping the shape at the room temperature excluding expansion, when an FRP structure is formed,
wherein the intermediate structure has a linear expansion coefficient larger than that of the FRP structure by $150 \times 10^{-6}$ (1/° C.) or more,
wherein a shape corresponding to the intermediate structure which has thermally expanded at the shaping temperature is formed between the layers of prepreg material, when the FRP structure is formed, and
wherein at the room temperature after the shaping of the FRP structure, the intermediate structure thermally shrinks to form a space between the intermediate structure and the layers of prepreg material due to shrinkage difference.

15. The artificial defect material according to claim 14, wherein the first intermediate structure is formed of a material selected from a group consisting of silicone rubber, silicone resin, fluororubber, natural rubber, butadiene rubber, styrene rubber, butyl rubber, nitrile rubber, ethylene propylene rubber, chlorosulfonated polyethylene rubber, and urethane rubber.

* * * * *